United States Patent [19]

Parkes et al.

[11] Patent Number: 5,152,982
[45] Date of Patent: Oct. 6, 1992

[54] COMPOSITIONS AND METHODS FOR FELV VACCINATION

[75] Inventors: Deborah Parkes, Oakland; Paul Luciw, Emeryville; Gary Van Nest, El Sobrante; Dino Dina, San Francisco, all of Calif.

[73] Assignee: Chiron Corporation, Emeryville, Calif.

[21] Appl. No.: 804,528

[22] Filed: Dec. 10, 1991

Related U.S. Application Data

[63] Continuation of Ser. No. 751,771, Jul. 2, 1985, abandoned, which is a continuation-in-part of Ser. No. 593,339, Mar. 26, 1984, abandoned, and a continuation-in-part of Ser. No. 647,966, Sep. 6, 1984, abandoned.

[51] Int. Cl.$^5$ .................... A61K 39/12; A61K 39/00; C12N 7/00
[52] U.S. Cl. ........................................ 424/89; 424/88; 435/235.1
[58] Field of Search .................. 424/89, 88; 435/235.1

[56] References Cited

U.S. PATENT DOCUMENTS

| | | | |
|---|---|---|---|
| 3,966,907 | 6/1976 | Jarrett et al. | 424/89 |
| 4,034,081 | 7/1977 | Jarrett et al. | 424/89 |
| 4,086,134 | 4/1978 | Jarrett et al. | 435/238 |
| 4,117,112 | 9/1978 | Jarrett et al. | 424/89 |
| 4,264,587 | 4/1981 | Pedersen | 424/89 |
| 4,332,793 | 6/1982 | Olson | 424/89 |
| 4,405,712 | 9/1983 | Vande Woude | |
| 4,406,885 | 9/1983 | Pinter | 424/88 |
| 4,434,157 | 2/1984 | Olsen | 435/153 |
| 4,663,436 | 5/1987 | Elder et al. | 424/88 |
| 4,701,416 | 10/1987 | Nunberg | 435/320 |
| 4,722,840 | 2/1988 | Valenzuela et al. | 424/88 |

FOREIGN PATENT DOCUMENTS 247904 12/1987 European Pat. Off. .

OTHER PUBLICATIONS

Panganeban et al., Nature, vol. 306, pp. 155–160, 1983.
Abraham Pinter et al., Virology, vol. 83, pp. 417–422 (1977).
Abraham Pinter et al., Virology, vol. 91, pp. 345–351 (1978).
Gerhard Hunsman et al., Virology, vol. 113, pp. 602–612 (1981).
Ronald A. Salerno et al., J. Nat'l Cancer Institute, vol. 61, pp. 1478–1493 (1978).
Mark G. Lewis et al., Infection and Immunity, vol. 34, pp. 888–894 (1981).
Emilio A. Emini et al., Nature, vol. 104, pp. 699–703 (1983).
Eckard Wimmer et al., Nature, vol. 308, p. 19 (1984).
Elwood Linney et al., Nature, vol. 308, pp. 470–472 (1984).
David Derse et al., Science, vol. 231, pp. 1437–1440 (1986).
Haralabos Paskalis et al., Proc. Nat'l. Acad. Sci. USA, vol. 83, pp. 6558–6562 (1986).
Barbara K. Felber et al., Science, vol. 229, pp. 675–679 (1985).
Craig A. Rosen et al., Cell, vol. 41, pp. 813–823 (1985).
James I. Mullins et al., Nucleic Acids Research, vol. 8, pp. 3287–3305 (1980).
Charles J. Sherr et al., Journal of Virology, vol. 34, pp. 200–212 (1980).
William J. DeLorbe et al., Journal of Virology, vol. 36, pp. 50–61 (1980).
Paul A. Luciw et al., Cell, vol. 33, pp. 705–716 (1983).
Antonito T. Panganiban et al., Nature, vol. 306, pp. 155–160 (1983).

Primary Examiner—Christine M. Nucker
Assistant Examiner—Lynette F. Smith
Attorney, Agent, or Firm—Spencer, Frank & Schneider

[57] ABSTRACT

Novel methods and compositions are provided for vaccinating a host susceptible to viral infection. Particularly, an initial injection is employed of one or more polypeptides associated with the host immune response to the pathogen followed by administration of the pathogen in attenuated form, particularly having a deletion associated with the gene expressing at least one of said polypeptides. In this manner, hosts may be vaccinated so as to maintain a strong defensive posture against infection from the pathogen. The method is specifically illustrated with feline leukemia virus.

13 Claims, 12 Drawing Sheets

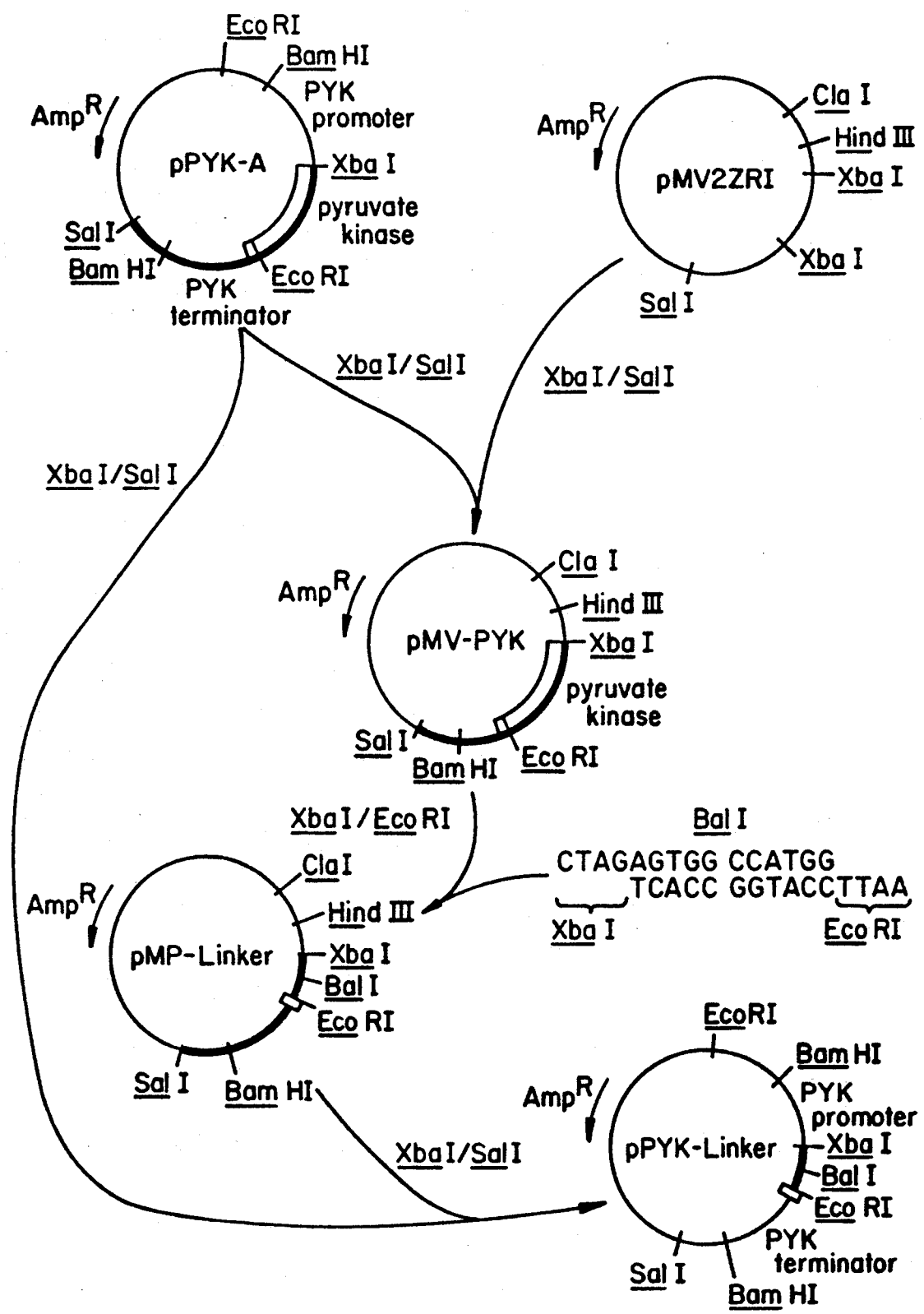
FIG._1A.

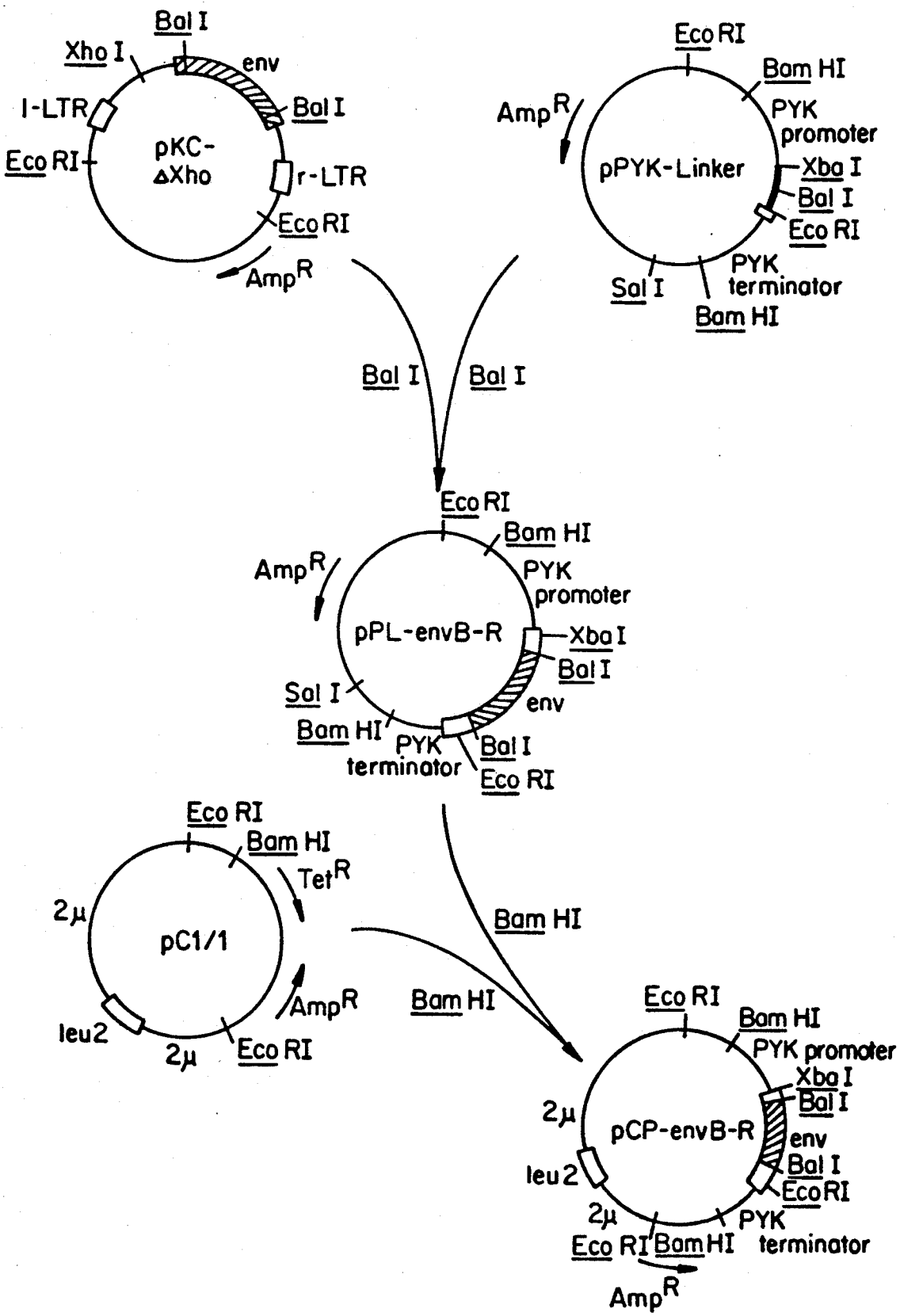
FIG._1B.

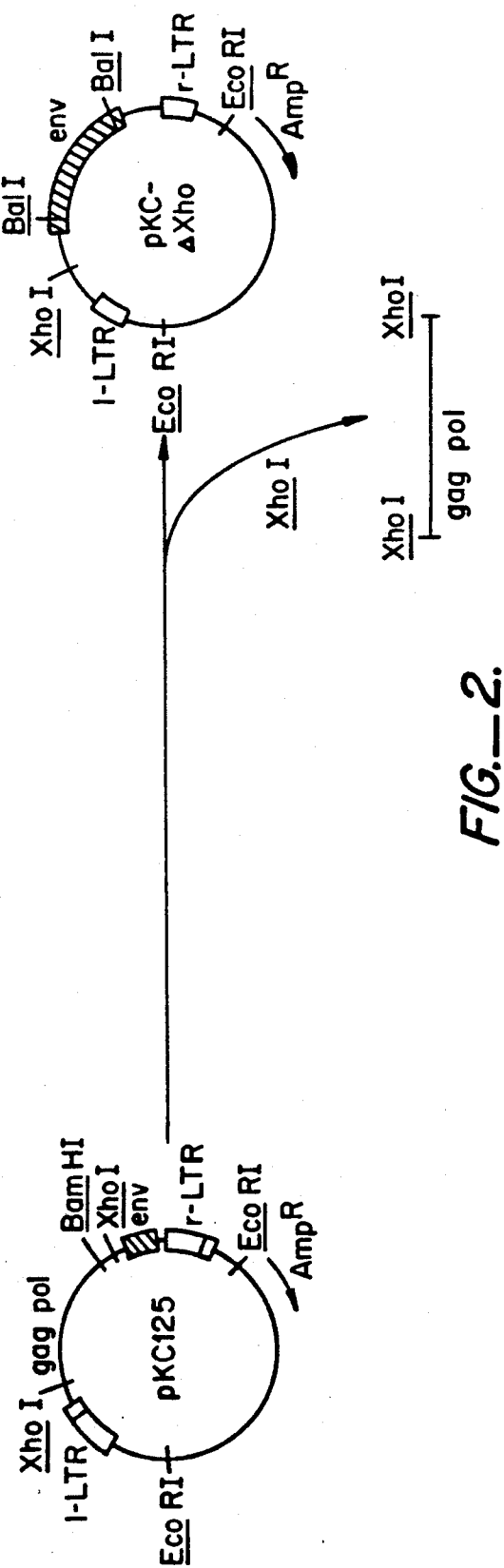
FIG._2.
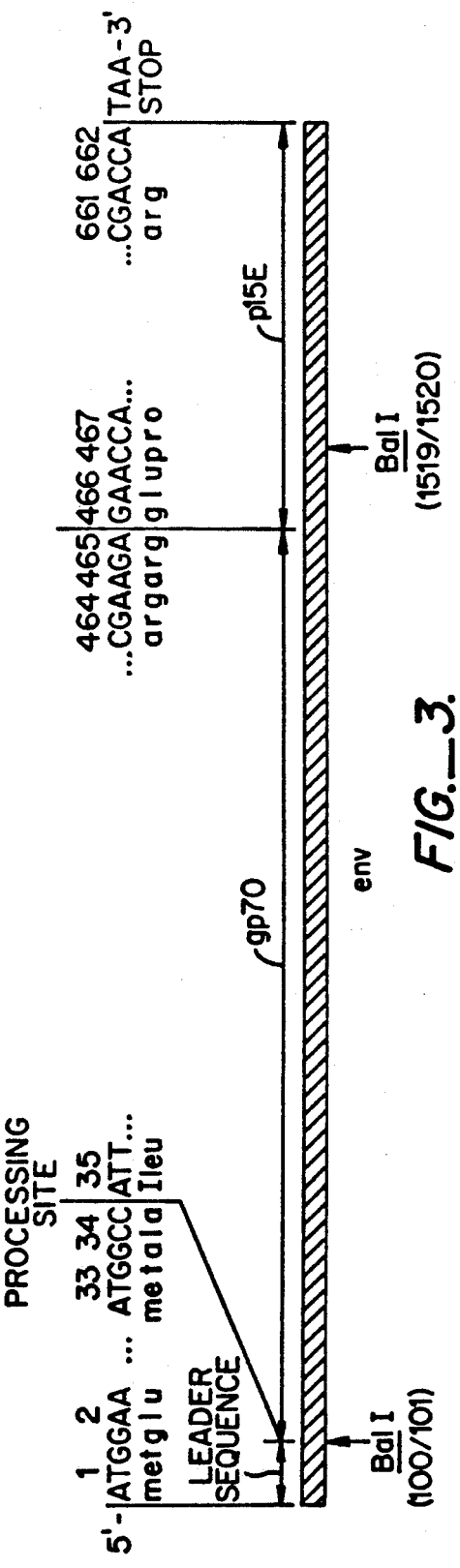
FIG._3.

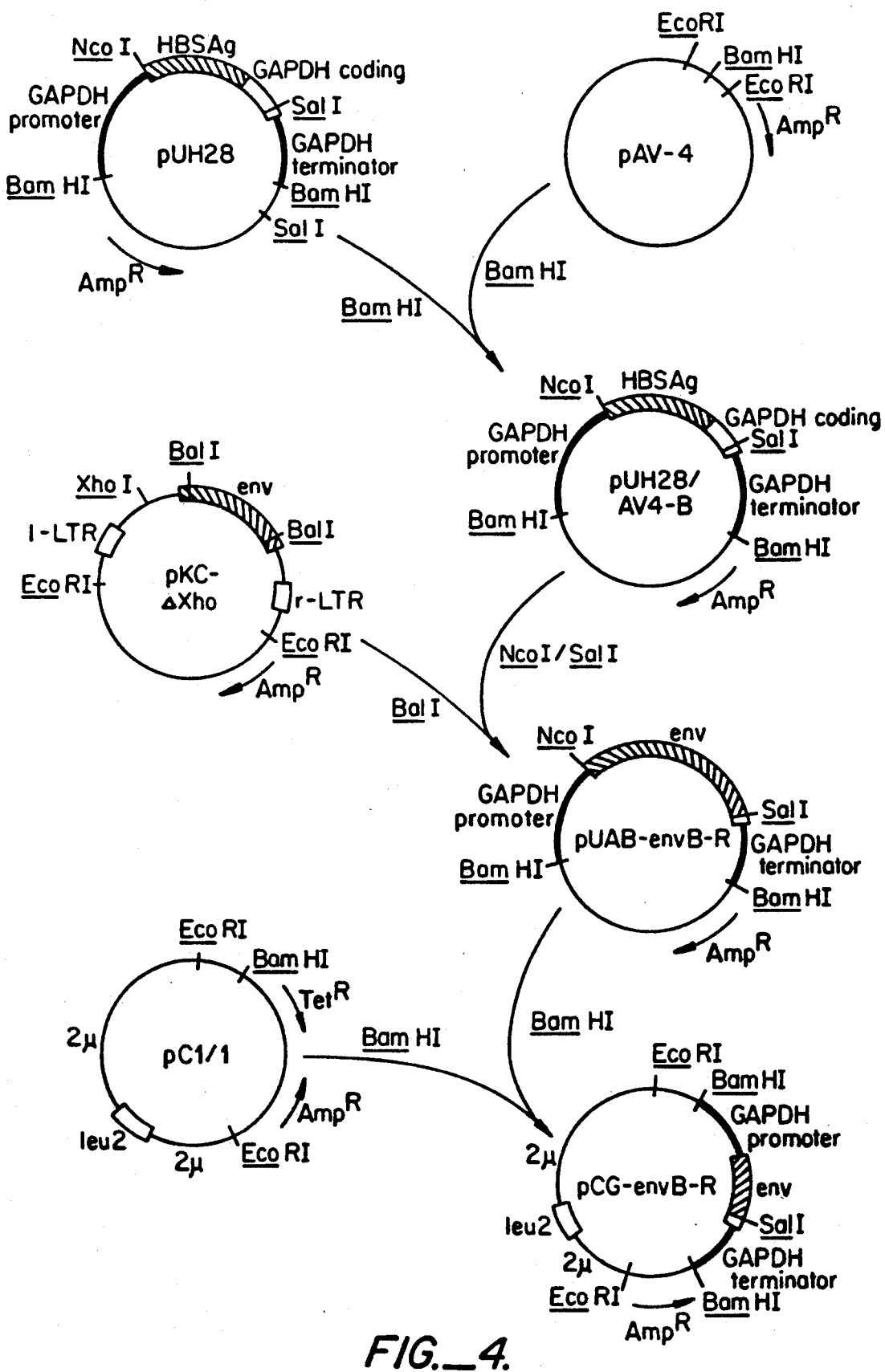
FIG._4.

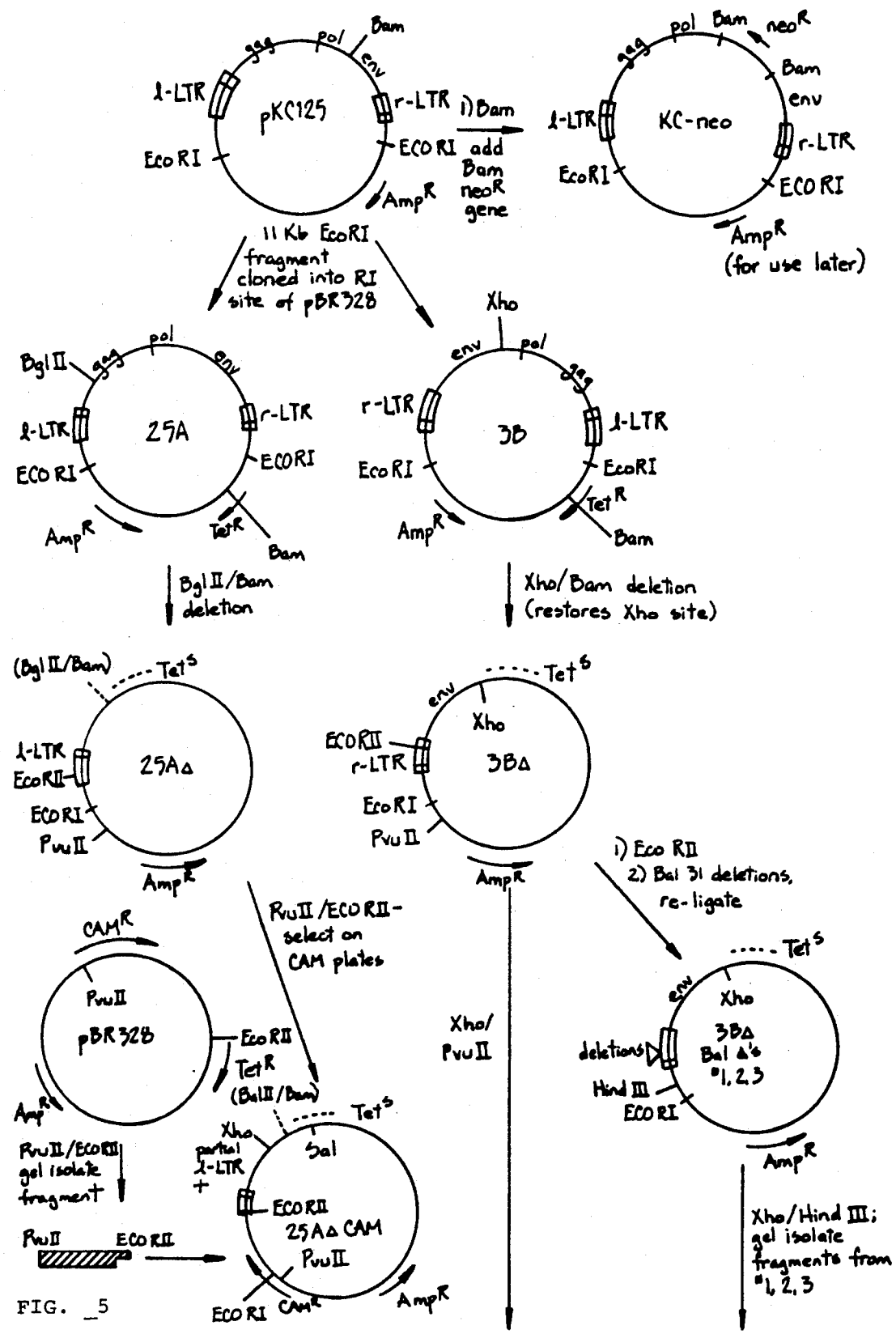
FIG. _5

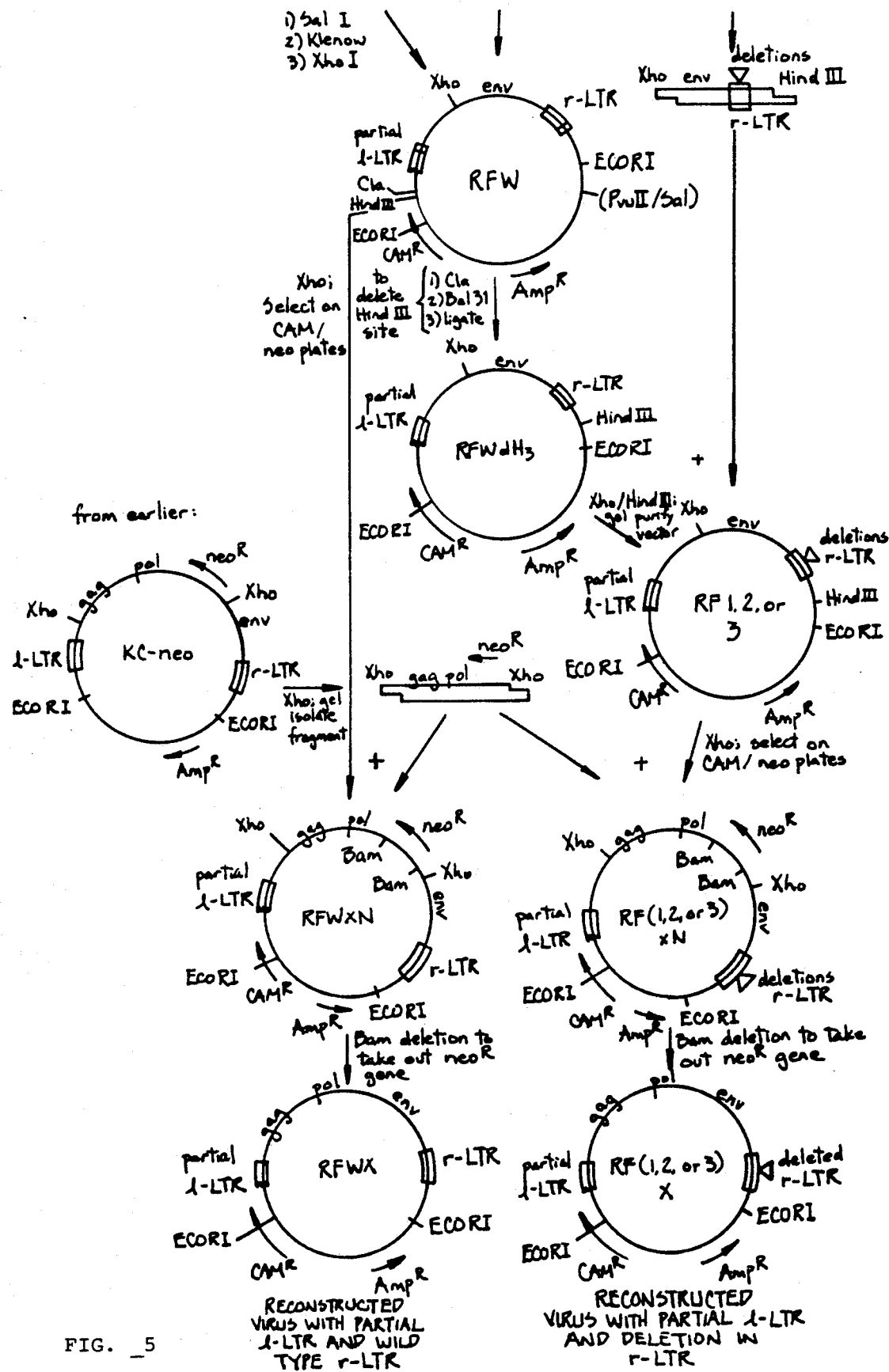
FIG. _5_

Nucleotide homology between Feline Leukemia Virus envelope gene of subgroups A, B and C in the region from HindIII in the polymerase gene to the 3'-terminus of the LTR. Asterisks (*) indicate homology between corresponding bases in the sequence of each subgroup. Colons indicate gaps that have been left in certain regions for purposes of alignment of the three sequences, to provide maximal homology. The translational initiation codon of the envelope protein (ATG) is boxed.

```
[C] AAGCTTACCCCGCCAAACATGAAACAGCAAAAGTTGTTGCCAAGAAACTCTTAGAAGAGATCTTTCCTCGTT
    ************************************* ******************** ** ***** ** *
[A] AAGCTTACCCCGCCAAACATGAAACAGCAAAAGTTGTCGCCAAGAAACTCTTAGAAGAAATTTTTCCCCGCT
    ************************************* **********************************
[B] AAGCTTACCCCGCCAAACATGAAACAGCAAAAGTTGTTGCCAAGAAACTCTTAGAAGAAATTTTTCCCCGCT

ACGGGATCCCTCAGGTATTGGGTTCGGATAATGGACCCGCCTTTATCTCCCAGGTAAGTCAGTCTGTGGCCA
    ********** ************ ************************************************
    ACGGGATCCCCCAGGTATTGGGTTCAGATAATGGACCCGCCTTTATCTCCCAGGTAAGTCAGTCTGTGGCCA
    ********** ************ ************************************************
    ACGGGATCCCGCAGGTATTGGGTTCAGATAATGGACCCGCCTTTATCTCCCAGGTAAGTCAGTCTGTGGCCA

CCCTACTGGGGATTAATTGGAAATTACATTGCGCATACCGACCCCAAAGTTCAGGTCAGGTAGAAAGAATGA
    ******************** ******* ***** *************************************
    CCCTACTGGGGATTAATTGGAAGTTACATTGTGCATACCGACCCCAAAGTTCAGGTCAGGTAGAAAGAATGA
    ********************************************************************* 
    CCCTACTGGGGATTAATTGGAAGTTACATTGTGCATACCGACCCCAAAGTTCAGGTCAGGTAGAAAGAATGA

ATAGATCAATTAAGGAGACTTTAACTAAATTAACGCTAGAAACTGGCTCTAAGGATTGGGTACTCCTCTTGC
    *********************************************************** ****** *** 
    ATAGATCAATTAAGGAGACTTTAACTAAATTAACGCTAGAAACTGGCTCTAAGGATTGGGTGCTCCTCCTGC
    ************************************************************************
    ATAGATCAATTAAGGAGACTTTAACTAAATTAACGCTAGAAACTGGCTCTAAGGATTGGGTGCTCCTCCTGC

CTTTGGTTTTATACCGGGTACGAAATACACCAGGTCCCCACGGGTTAACCCCTTTTGAAATCCTGTACGGGG
    *   ******************  ** **  **** ** ********** ****  ****************
    CCCTGGTTTTATACCGGGTACGTAACACGCCGGGTCCCCACGGGTTAACTCCTTTTGAAATCCTGTACGGGG
    ************************************** ********************************
    CCCTGGTTTTATACCGGGTACGTAACACGCCAGGCCCCCACGGGTTAACTCCTTTTGAAATCCTGTACGGGG

CACCCCCACCTCTGGCTCACTTTTTCGATGCTGACATCTCTAGCTTTGCTACCTCCCCCACTATGCAGGCAC
    *********** * ******** * ************ ********* ************************
    CACCCCCACCTATGGCTCACTTCTTTGATGCTGATATCTCTAGCTTCGCTACCTCCCCCACTATGCAGGCAC
    *********** * ******** * ** **** ****  ***** ***************************
    CACCCCCACCTATGGCTCACTTCTTTGATACTGATATCTCTCGTATCGCTACCTCCCCCACTATGCAGGCAC

ATTTACGCGCCCTGCAGCTGGTCCAAGAAGAGATCCAGAGACCTCTAGCGGCAGCCTACCGAGAAAGGCTCC
    *********************************** ************** ****** ***** **** 
    ATTTACGCGCCCTGCAGCTGGTCCAAGAAGAGATCCGGAGACCTCTAGCGGCGGCCTACCAAGAAAAGCTCG
    ************************************************** ****** ***********
    ATTTACGCGCCCTGCAGCTGGTCCAAGAAGAGATCCAGAGACCTCTAGCGGCGGCCTACCGAGAAAAGCTCG

AAACCCCGGTTGTGCCTCACCCCTTCAAACCAGGAGACTCCGTCTGGGTGCGGAGACATCAAACCAAGAACC
    ****************************************************** ****************
    AAACCCCGGTTGTGCCTCACCCCTTCAAACCAGGAGACTCCGTCTGGGTTCGGAGACATCAAACCAAGAACC
    ************************************************************************
    AAACCCCGGTTGTGCCTCACCCCTTCAAACCAGGAGACTCCGTCTGGGTTCGGAGACATCAAACCAAGAACC

TCGAGCCACGGTGGAAAGGACCACATATCGTCCTCCTGACCACCCCCACAGCCTTAAAGGTAGACGGAGTTG
    ************************************************************************
    TCGAGCCACGGTGGAAAGGACCACATATCGTCCTCCTGACCACCCCCACAGCCTTAAAGGTAGACGGAGTTG
    ************************************************************************
    TCGAGCCACGGTGGAAAGGACCACATATCGTCCTCCTGACCACCCCCACAGCCTTAAAGGTAGACGGAGTTG

CTGCTTGGATTCACGCCTCCCACGTGAAAGCTGCAGGACCAACCACCGATCAGGACCTCCCGAACGACCCTA
    ****  ******************************************  **** *** ** *** *
    CTGCCTGGATTCACGCCTCTCACGTGAAAGCTGCAGGACCAACCACCAATCAAGACCTCTCGGACAGCCCCA
    ************************************************************************
    CTGCCTGGATTCACGCCTCTCACGTGAAAGCTGCAGGACCAACCACCAATCAAGACCTCTCGGACAGCCCCA
```

FIG. 6

```
GCTCAGACGATCCATCAAGATGGAAAGTCCAACGCACCCAAAACCCTCTAAAGATAAGACTTTCCCGTGGAA
*********************  *************************************** *  *******
GCTCAGACGATCCATCAAGATGGAAAGTCCAACGCACCCAAAACCCTCTAAAGATAAGACTCTCTCGTGGAA
*********************  *************************************************
GCTCAGACGATCCATCAAGATGGAAAGTCCAACGCACCCAAAACCCTCTAAAGATAAGACTCTCTCGTGGAA

CTTAGTGTTTCTGGTGGGGATCTTATTCCAAATAGATATGGGAATGGCCAATCCTAGCCCACACCAAGTATA
*****  *************** ***** **  ******** ***************** ****** ****
CTTAGCGTTTCTGGTGGGGATCTTATTTACAATAGACATAGGAATGGCCAATCCTAGTCCACACCAAATATA
*****  *********************  *******************************  ******  
CTTAGTGTTTCTGGTGGGGATCTTATTCACAATAGACATAGGAATGGCCAATCCTAGTCCGCACCAAGTGTA

TAATGTAACTTGGGTAATAACCAATGTACAAACCAACTCCCGAGCTAATGCCACTTCTATGTTAGGAACCTT
*************************  *** ****** ***** ***** *************** *****
TAATGTAACTTGGGTAATAACCAATGTACAAACTAACACCCAAGCTAACGCCACCTCTATGTTAGGAACCTT
*********  ********  *****  ****  ****    ******** ***** **** ********
TAATGTAACTTGGACAATAACCAACCTTGTAACTGGAACAAAGGCTAATGCCACCTCCATGTTGGGAACCCT

AACCGATGCCTACCCTACCCTATATGTTGATTTATGTGACCTAGTGGGAGACACCTGGGAACCTATAGCCCC
*****************   ******** ****************************************** **
AACCGATGCCTACCCTACCCTACATGTTGACTTATGTGACCTAGTGGGAGACACCTGGGAACCTATAGTCCT
** **  ****   ***********  ** * *** *  ** *** * ***   *** *** **  *  *
GACAGACGCCTTCCCTACCATGTATTTTGACTTATGTGATATAATAGGAAATACATGGAACCCTTCAGATCA

AGACCCA:::::::::::AGATCTTGGGCACGTTATTCCTCCTCAACACATGGATGCAAAACTACAGATAGAAA
* *****               ** *** *************** *******  * * ****************
AAACCCAACCAATGTAAAACACGGGGCACGTTACTCCTCCTCAAAATATGGATGTAAAACTACAGATAGAAA
* ***                                     *                *************
GGAACCA::::::::::::::::::::::::::::::::::TTCCCAGGGTATGGATGTGATCAGCCTATGAGGAG

AAAACAGCAACAAACATACCCCTTTTATGTCTGCCCAGGGCATGCCCCCTCGATGGGGCCTAAGGGAACATA
************ ***** **************  ***** ************** ****** ********* *
AAAACAGCAACAGACATACCCCTTTTACGTCTGCCCCGGACATGCCCCCTCGTTGGGGCCAAAGGGAACACA
** **  *   ********** *****   **  ********   **** ** ****      ** ** **
GTGGCAACAGAGAAACACACCCTTTTATGTCTGTCCAGGACATGCC:::::::::::::::AACCGGAAGCA

TTGTGGAGGGGCACAAGATGGGTTTTTGTGCCGCATGGGGATGTGAAACCACCGGAGAGGCTTGGTGGAAGCC
************************************** **** **************  ************
TTGTGGAGGGGCACAAGATGGGTTTTTGTGCCGCATGGGGATGTGAGACCACCGGAGAAGCTTGGTGGAAGCC
****   *** ********  ** ** * ***** ** *****   **  ****     *  * *  ** **
ATGTGGGGGCCACAAGATGGGTTCTGCGCTGTATGGGGTTGCGAGACCACCGGGGAAACCTATTGGAGACC

CACCTCCTCATGGGACTATATCACAGTAAAAAGAGGAAGTAATCAG:::::::::::::::::::::::::
**************************************   ****    
CACCTCCTCATGGGACTATATCACAGTAAAAAGAGGGAGTAGTCAG:::::::::::::::::::::::::
**************  *********  **  ** ****   ****
CACCTCCTCATGGGACTACATCACAGTAAAAAAAGGGGTTACTCAGGGAATATATCAATGTAGTGGAGGTGG

:::::::::::::::::::::::::::::::::::::::::::::::::GACAATAGCTGTAAGGGCAAATGTAA
                                                   ********** **** ***** **
:::::::::::::::::::::::::::::::::::::::::::::::::GACAATAGCTGTGAGGGAAAATGCAA
                                                         *  * ***   *****
TTGGTGTGGGCCCTGTTACGATAAAGCTGTTCACTCCTCGACAACGGGAGCTAGTGAAGGGGGCCGGTGCAA

CCCCCTGGTCTTGCAGTTCACCCAGAAGGGAAGACAAGCCTCTTGGGACAGACCTAAAATGTGGGGGCTACG
*******  * ****** ****************************** *********  ***** * *  **
CCCCCTGGTTTTGCAGTTCACCCAGAAGGGAAGACAAGCCTCTTGGGACGGACCTAAGATGTGGGGATTGCG
****  *  * *****   *** *****************  ********    ***** *****  * ***
CCCCTTGATCTTGCAATTTACCCAAAAGGGAAGACAAACATCTTGGGATGGACCTAAGTCATGGGGGCTACG

ACTATACCGTTCAGGATATGACCCTATAGCCCTGTTCTCGGTATCCCGGCAAGTAATGACCATTACGCCGCC
**********  ***************  *     **  *** ** ********   *************  **
ACTATACCGTACAGGATATGACCCTATCGCTTTATTCACGGTGTCCCGGCAGGTATCAACCATTACGCCGCC
*********   **************** *  * ***  **** *********    **************
ACTATACCGTTCAGGATATGACCCTATAGCCCTGTTCTCGGTATCCCGGCAAGTAATGACCATTACGCCGCC

TCAGGCGATGGGACCCAACTTAGTCTTACCTGATCAAAAACCCCCATCCCGACAATCTCAAACAAAGTCCAA
****** ********  ***  *** ** *** ********************* ************ *****
TCAGGCAATGGGACCAAAACCTAGTCTTACCTGATCAAAAACCCCCATCCCGACAATCTCAAACAGGGTCCAA
*****   **********  *** *  ***********************   ***********   *  
TCAGGCATGGGACCAAATCTAGTCCTGCCTGATCAAAAACCCCCATCCAGGCAATCTCAAATAGAGTCCCG

GGTGACAACCCAGAGGCCCCAAATAACTAGCAGCACCCCAAGG:::::::::::::::::::TCTGTCGCCTC
*** * ***********          * *   *** ********                 ***** *** *
AGTGGCGACCCAGAGGCCCCAAACGAATGAAAGCGCCCCAAGG:::::::::::::::::::TCTGTTGCCCC
***  * *  **   ****** *   *****                                  *  
AGTAACACCTCACCATTCCCAAGGCAACGGAGGCACCCCAGGTATAACTCTTGTTAATGCCTCCATTGCCCC

C:::::::::::::::GCTACCATGGGTCCCAAACGGATAGGGACCGGAGATAGATTAATAAATTTAGTGCA
*                ****** ************ *  ********* ************** **** *
C:::::::::::::::ACCACCATGGGTCCCAAACGGATTAGGACCGGAGATAGGTTAATAAATTTAGTACA
                 ***  ************************ * ************************
TCTAAGTACCCCTGTCACCCCCGCAAGTCCCAAACGGATTGGGACCGGAGATAGGTTAATAAATTTAGTACA

AGGGACATACCTAGCCTTAAATGCCACCGACCCCAACAAAACTAAAGACTGTTGGCTCTGCCTGGTTTCTCG
**********************************************************************
AGGGACATACCTAGCCTTAAATGCCACCGACCCCAACAAAACTAAAGACTGTTGGCTCTGCCTGGTTTCTCG
******  *****************************  ****************** ** ***********
AGGGACATACCTAGCCTTAAATGCCACCGACCCCAACAGAACTAAACACTGTTGGCTCTGCCTGGTTTCTCG
```

FIG. 6

```
ACCACCTTATTACGAAGGGATTGCAGTCTTAGGTAACTACAGCAACCAAACAAACCCCCCCCCATCCTGCCT
*****  ******** ********* ********************************************
ACCACCCTATTACGAAGGGATTGCAATCTTAGGTAACTACAGCAACCAAACAAACCCCCCCCCATCCTGCCT
************************************************************************
ACCACCCTATTACGAAGGGATTGCAATCTTAGGTAACTACAGCAACCAAACAAACCCCCCCCCATCCTGCCT

ATCTACCCCGCAACATAAACTGACTATATCAGAAGTGTCCGGGCAAGGTTTGTGCATAGGGACTGTTCCTAA
*****  ********  ***** **  ***** ** *******  ***********************
ATCTATTCCGCAACACAAACTAACCATATCTGAAGTATCAGGGCAAGGACTGTGCATAGGGACTGTTCCTAA
************************************************************************
ATCTATTCCGCAACACAAACTAACCATATCTGAAGTATCAGGGCAAGGACTGTGCATAGGGACTGTTCCTAA

GACCCACCAAGCTTTGTGCAAAAAGACACAAAAAGGACATAAAGGGACTCACTACCTGGCAGCCCCCAACGG
*********  ******* *******  ****** * ******* **   *****  ** ********
GACCCACCAGGCTTTGTGCAATGAGACACAACAGGGACATACAGGGGCGCACTATCTAGCCGCCCCCAACGG
************************************************************** *********
GACCCACCAGGCTTTGTGCAATGAGACACAACAGGGACATACAGGGGCGCACTATCTAGCCGCCCCCAATGG

CACCTATTGGGCCTGTAACACTGGACTCACCCCATGCATTTCCATGGCAGTGCTCAATTGGACCTCTGATTT
***********************************************  *********************
CACCTATTGGGCCTGTAACACTGGACTCACCCCATGCATTTCCATGGCGGTGCTCAATTGGACCTCTGATTT
***********************************************  *********************
CACCTATTGGGCCTGTAACACTGGACTCACCCCATGTATTTCCATGGCGGTGCTCAATTGGACCTCTGATTT

TTGTGTCTTAATCGAATTATGGCCCAGAGTAACCTACCATCAACCCGAATATATTTACACACATTTCGACAA
******************************  *****************  * *********** * ***
TTGTGTCTTAATCGAATTATGGCCCAGAGTGACTTACCATCAACCCGAATATGTGTACACACATTTTGCCAA
************************************************************************
TTGTGTCTTAATCGAATTATGGCCCAGAGTGACTTACCATCAACCCGAATATGTGTACACACATTTTGCCAA

AGCTGTCAGGTTCCGAAGAGAACCTATATCACTAACCGTTGCCCTTATGTTGGGAGGACTCACCGTAGGGGG
***************************  ********** ****************** ** ********
AGCTGTCAGGTTCCGAAGAGAACCAATATCACTAACCGTTGCCCTTATGTTGGGAGGACTTACTGTAGGGGG
*****  ***************  *** ** *** ** ** ****  ******  *** * * *******
AGCTGCAGGTTCCGAAGAGAACGAATATCACTAAGTGTTGCCCTCATGTTGGAGGACTCACTGTAGGGGG

CATAGCCGCGGGGGTCGGAACAGGGACTAAAGCCCTCCTTGAAACAGCCCAGTTCAGACAACTACAAATAGC
********************************************************************* **
CATAGCCGCGGGGGTCGGAACAGGGACTAAAGCCCTCCTTGAAACAGCCCAGTTCAGACAACTACAAATGGC
************************************************************************
CATAGCCGCGGGGGTCGGAACAGGGACTAAAGCCCTCATTGAAACAGCCCAGTTCAGACAACTACAAATGGC

CATGCACACAGACATCCAGGCCCTGGAAGAGTCAATTAGTGCCTTAGAAAAATCCCTGACCTCCCTCTCTGA
***************** ****  ***** ****************** *************** *****
CATGCACACAGACATCCAGGCCCTAGAAGAATCAATTAGTGCCTTAGAAAAGTCCCTGACCTCCCTTTCTGA
************************************************************************
CATGCACACAGACATCCAGGCCCTAGAAGAGTCAATTAGTGCCTTAGAAAAGTCCCTGACCTCCCTTTCTGA

GGTAGTCCTACACAATAGGCGGGGCCTAGATATTCTGTTCTTACAAGAGGGAGGGCTCTGTGCCGCATTAAA
 ******  ***  ** ************ ****** ************************ ********
AGTAGTCTTACAAAACAGACGGGGCCTAGATATTCTATTCTTACAAGAGGGAGGGCTCTGTGCCGCATTGAA
***************************   ****************************************
AGTAGTCTTACAAAACAGACGGGGCCTGGATATTCTATTCTTACAAGAGGGAGGGCTCTGTGCCGCATTAAA

AGAAGAATGCTGCTTCTATGCAGATCACACCGGACTCGTCCGAGACAATATGGCTAAATTAAGAGAAAGACT
*********  ************ *************************************************
AGAAGAATGTTGCTTCTATGCGGATCACACCGGACTCGTCCGAGACAATATGGCTAAATTAAGAGAAAGACT
************************************************************************
AGAAGAATGTTGCTTCTATGCGGATCACACCGGACTTGTCCGAGACAATATGGCTAAATTAAGAGAAAGACT

AAAACAGCGGCAACAACTGTTTGATTCCCAACAGGGATGGTTTGAAGGATGGTTCAACAAGTCCCCCTGGTT
*****************  **** ************************************************
AAAACAGCGGCAACAACTGTTTGACTCCCAACAGGGATGGTTTGAAGGATGGTTCAACAAGTCCCCCTGGTT
************************************************************************
AAAACAGCGGCAACAACTGTTTGACTCCCAACACGGATGGTTTGAAGGATGGTTCAACAAGTCCCCCTGGTT

TACAACCCTAATTTCCTCCATCATGGGCCCCTTACTAATCCTACTCCTAATTCTCCTCCTCGGCCCATGCAT
**********************  *********************************  *************
TACAACCCTAATTTCCTCCATTATGGGCCCCTTACTAATCCTACTCCTAATTCTCCTCTTCGGCCCATGCAT
************************************************************************
TACAACCCTAATTTCCTCCATTATGGGCCCCTTACTAATCCTACTCCTAATTCTCCTCTTCGGCCCATGCAT

CCTTAACCGATTAGTGCAATTCGTAAAAGACAGAATATCTGTGGTACAAGCCTTAATTTTAACCCAACAGTA
************ ** ************************************ ** ****************
CCTTAACCGATTAGTACAATTCGTAAAAGACAGAATATCTGTGGTACAGGCTTTAATTTTAACCCAACAGTA
******  ****************************************************************
CCTTAACAGATTAGTACAATTCGTAAAAGACAGAATATCTGTGGTACAAGCCTTAATTTTAACCCAACAGTA

CCGACAGATACAACAATACGATTCGGACCGACCATGATTTCCAATTAAATGTATGATTCCATTTAGTCCCTA
** ******* *** ***** * ******************************************** ****
CCAACAGATAAAGCAATACGATCCGGACCGACCATGATTTCCAATTAAATGTATGATTCCATTTAGTCCCCA
************************ *******************************************  **
CCAACAGATAAAGCAATACGATCCGGACCGACCATAATTTCCAATTAAATGTATGATTCCATTTAGTCTCCA

GAAGAAGGGGGAAATGAAAGACCCCCCCCCCACCCCAAAACTTAGCCAGCTACTGCAGCAATGCCATTTCA
*** ********* *  **  ****                 ***************** **  *******
GAAAAAGGGGGGATGAAAGACCCCCT:::::ACCCCAAAATTTAGCCAGCTACTGCAGTGGTGTCATTTCA
**************  ***********     ****************************  ********
GAAAAAGGGGGAATGAAAGACCCCCT:::::ACCCCAAAATTTAGCCAGCTATTGCAGTGGTGCCATTTCA
```

FIG. 6

```
CAAGGAATGGAAAATTACCCAAACATGTTCCCATGAGATATAAGGAAGTTAGGGGCTAAAACAGGATATCTG
**** *********** *** ******************************** ******************
CAAGGCATGGAAAATTACTCAAGTATGTTCCCATGAGATATAAGGAAGTTAGAGGCTAAAACAGGATATCTG
************************************************ ***********************
CAAGGCATGGAAAATTACTCAAGTATGTTCCCATGAGATACAAGGAAGTTAGAGGCTGAAACAGGATATCTG

TGGTTAAGCACCTGGGCCCCGGCTTAAAGCCAAGAACAGTTAAGCCTCGGATATAGCTGAAACAGCAGAAGT
********************* ** *************** ** *************************
TGGTTAAGCACCTGGGCCCCGGCTTGAGGCCAAGAACAGTTAAACCCCGGATATAGCTGAAACAGCAGAAGT
************************************************ ********************
TGGTTAAGCACCTGGGCCCCGGCTTGAGGCCAAGAACAGTTAAACCCCC:ATATAGCTGAAACAGCAGAAGT

TTCAAGGCCACTGCCAGCAGTCTCCAGGCTCCCCAGTTGACCAGAGTTCAACCTTCCGCCTCATTTAAACTA
********* *************************************** *******************
TTCAAGGCCGCTGCCAGCAGTCTCCAGGCTCCCCAGTTGACCAGAGTTCGACCTTCCGCCTCATTTAAACTA
*********************************************** *******************
TTCAAGGCCGCTGCCAGCAGTCTCCAGGCTCCCCAGTTGACCAGAGTTCGACCTTCCGCCTCATTTGAACTA

ACCAATCCCCACGCTTCTCGCTTCTGTACGCGCGCTTTCTGCTATAAAATGAGCCATCAGCCCCCACCGGGC
************** ************ *********************** ****************
ACCAATCCCCACGCCTCTCGCTTCTGTGCGCGCGCTTTCTGCTATAAAACGAGCCATCAGCCCCCAACGGGC
*********************************************** ******************
ACCAATCCCCACGCCTCTCGCTTCTGTGCGCGCGCTTTCTGCTATAAAACGAGCCCTCAGCCCCCAACGGGC

GCGCAAGTCTTTGCTGAGACTTGACCGCCCCGGGTACCCGTGTACCGAATAAACCTCTTGCTGTTTGCATCT
****************************************** ***************** ********
GCGCAAGTCTTTGCTGAGACTTGACCGCCCCGGGTACCCGTGTAGCGAATAAACCTCTTGCTGATTGCATCT
************************************************ ********** *********
GCGCAAGTCTTTGCTGAGACTTGACCGCCCCGGGTACCCGTGTA:CGAATAAACCTCTTGCTGTTTGCATCT

GACTCGTGGTCTCGGTGTTCCGTGGGCACGGGGTCTCATCGCCGAGGAAGACCTAGTTCGGGGGTCTTTCA
**** ****************************************************************
GACTTGTGGTCTCGGTGTTCCGTGGGCACGGGGTCTCATCGCCGAGGAAGACCTAGTTCGGGGGTCTTTCA
**** ****************************************************************
GACTCGTGGTCTCGGTGTTCCGTGGGTACGGGGTCTCATCGCCGAGGAAGACCTAGTTCGGGGGTCTTTCA
```

FIG. _6

Protein sequence homology between Feline Leukemia envelope protein of subgroups A, B and C. Amino acids are indicated using the one letter code. Asterisks indicate homology between corresponding amino acids in each subgroup. "XXXXXXXXX" indicate gaps that have been left in certain regions for purposes of alignment of the three amino acid sequences to provide maximal homology.

```
[C]  MESPTHPKPSKDKTFPWNLVFLVGILFQIDMGMANPSPHQVYNVTWVITNVQTNSRANAT
     **************- ***|******* **-**********|***************-****
[A]  MESPTHPKPSKDKTLSWNLAFLVGILFTIDIGMANPSPHQIYNVTWVITNVQTNTQANAT
     ************** |****************|*********- * * *****
[B]  MESPTHPKPSKDKTLSWNLVFLVGILFTIDIGMANPSPHQVYNVTWTITNLVTGTKANAT

[C]  SMLGTLTDAYPTLYVDLCDLVGDTWEPIAPDPXXXRSWARYSSSTHGCKTTDRKKQQQTY
     ***************|**************- * ****** ************
[A]  SMLGTLTDAYPTLHVDLCDLVGDTWEPIVLNPTNVKHGARYSSSKYGCKTTDRKKQQQTY
     ********-**-|-****--* ** *          ****  *- ***
[B]  SMLGTLTDAFPTMYFDLCDIIGNTWNPSDXXXXXXXXXXQEPFGYGCDQPMRRWQQRNT

[C]  PFYVCPGHAPSMGPKGTYCGGAQDGFCAAWGCETTGEAWWKPTSSWDYITVKRGSNQXXX
     *********-***** ******************************** *
[A]  PFYVCPGHAPSLGPKGTHCGGAQDGFCAAWGCETTGEAWWKPTSSWDYITVKRGSSQXXX
     *********     *** ******-********* -*-**********-* -*
     PFYVCPGHAXXXXXNRKQCGGPQDGFCAVWGCETTGETYWRPTSSWDYITVKKGVTQGIY

[C]  XXXXXXXXXXXXXXXXXXXXXXDNSCKGKCNPLVLQFTQKGRQASWDRPKMWGLRLYRSGY
     **** ***************  *****    *******+*
[A]  XXXXXXXXXXXXXXXXXXXXXXDNSCEGKCNPLVLQFTQKGRQASWDGPKMWGLRLYRTGY
     * *-****-*********** ****** *******-**
[B]  QCSGGGWCGPCYDKAVHSSTTGASEGGRCNPLILQFTQKGRQTSWDGPKSWGLRLYRSGY

[C]  DPIALFSVSRQVMTITPPQAMGPNLVLPDQKPPSRQSQTKSKVTTQRPQITSSTPRXXXX
     ******-***********************************   ***|******  *|**
[A]  DPIALFTVSRQVSTITPPQAMGPNLVLPDQKPPSRQSQTGSKVATQRPQTNESAPRXXXX
     ******-****-************************ *-*| - * *  *
[B]  DPIALFSVSRQVMTITPPQAMGPNLVLPDQKPPSRQSQIESRVTPHHSQGNGGTPGITLV

[C]  XXSVASXXXXXATMGPKRIGTGDRLINLVQGTYLALNATDPNKTKDCWLCLVSRPPYYEG
       ***            *************************-****-*********
[A]  XXSVAPXXXXXTTMGPKRIGTGDRLINLVQGTYLALNATDPNRTKDCWLCLVSRPPYYEG
     *-**   *  -                **********************  ***********
[B]  NASIAPLSTPVTPASPKRIGTGDRLINLVQGTYLALNATDPNRTKHCWLCLVSRPPYYEG

[C]  IAVLGNYSNQTNPPPSCLSTPQHKLTISEVSGQGLCIGTVPKTHQALCKKTQKGHKGTHY
     **-*********************** ****************** ** ** * **
[A]  IAILGNYSNQTNPPPSCLSIPQHKLTISEVSGQGLCIGTVPKTHQALCNETQQGHTGAHY
     ************************************************************
[B]  IAILGNYSNQTNPPPSCLSIPQHKLTISEVSGQGLCIGTVPKTHQALCNETQQGHTGAHY

[C]  LAAPNGTYWACNTGLTPCISMAVLNWTSDFCVLIELWPRVTYHQPEYIYTHFDKAVRFRR
     ***************************************************-**** *******
[A]  LAAPNGTYWACNTGLTPCISMAVLNWTSDFCVLIELWPRVTYHQPEYVYTHFAKAVRFRR
     ************************************************************
[B]  LAAPNGTYWACNTGLTPCISMAVLNWTGDFCVLIELWPRVTYHQPEYVYTHFAKAARFRR
```

FIG. _7

```
[C]  EPISLTVALMLGGLTVGGIAAGVGTGTKALLETAQFRQLQIAMHTDIQALEESISALEKS
     ***********************************-**********************
[A]  EPISLTVALMLGGLTVGGIAAGVGTGTKALLETAQFRQLQMAMHTDIQALEESISALEKS
     ***************************-******************************
[B]  EPISLTVALMLGGLTVGGIAAGVGTGTKALIETAQFRQLQMAMHTDIQALEESISALEKS

[C]  LTSLSEVVLHNRRGLDILFLQEGGLCAALKEECCFYADHTGLVRDNMAKLRERLKQRQQL
     *********************************************************
[A]  LTSLSEVVLQNRRGLDILFLQEGGLCAALKEECCFYADHTGLVRDNMAKLRERLKQRQQL
     *********************************************************
[B]  LTSLSEVVLQNRRGLDILFLQEGGLCAALKEECCFYADHTGLVRDNMAKLRERLKQRQQL

[C]  FDSQQGWFEGWFNKSPWFTTLISSIMGPLLILLLILLLGPCILNRLVQFVKDRISVVQAL
     **** *******************************************************
[A]  FDSQQGWFEGWFNKSPWFTTLISSIMGPLLILLLILLFGPCILNRLVQFVKDRISVVQAL
     **** *******************************************************
[B]  FDSQHGWFEGWFNKSPWFTTLISSIMGPLLILLLILLFGPCILNRLVQFVKDRISVVQAL

[C]  ILTQQYQQIKQYDPDRP
     *****************
[A]  ILTQQYQQIKQYDPDRP
     *****************
[B]  ILTQQYRQIQQYDSDRP
```

FIG. _7

COMPOSITIONS AND METHODS FOR FELV VACCINATION

BACKGROUND OF THE INVENTION

1. Field of the Invention

Despite the extraordinary advances which have been made in the last five years in elucidating the immune process, the manner in which the immune process responds to a pathogen is still largely unexplained. There is still uncertainty as to why various pathogens may repeatedly and successfully be able to infect a host for extended periods of time before the infection is finally overcome, frequently requiring external help through the administration of antibiotics or other drugs.

Vaccines have been known for a long time and have found wide use in providing protection from an extended list of pathogen-caused disease. Nevertheless, despite this success, there still remain questions as to the best manner of administration, what elicits a response which will provide protection from infection, and whether individual or combinations of immunogens may be employed.

The protection from the disease appears to be related to eliciting a "strong" immune response, desirably without the significant affects associated with the disease. For vaccines to prove useful, it is usually necessary that one observe that a high antibody titer is obtained of antibodies associated with binding to the proteins of the pathogen. There is a continuing interest in the development of safe and effective vaccines, which will protect the host against a pathogenic invasion.

2. Brief Description of the Relevant Literature

Emini et al., *Nature* (1983) 104:699-703, reports employing a synthetic peptide as a primer for induction of anti-polio virus neutralizing antibodies resulting from the subsequent infection with the polio virus. Wimmer et al., *Nature* (1984) 308:19, describes the use of viral structural proteins as vaccines. See also, U.S. application Ser. Nos. 593,339 and 647,966, filed Mar. 26, 1984, and Sept. 6, 1984, respectively, whose disclosure is incorporated herein by reference.

SUMMARY OF THE INVENTION

Novel methods and compositions are provided for vaccinating mammalian hosts against viral infection by providing an initial inoculation of a composition including at least one envelope protein of a viral pathogen, followed by a second inoculation at a reasonable interval of an attenuated mutant of the viral pathogen. Particularly, at least one envelope protein or immunogenic fragment thereof is employed in a first vaccination, followed by a second vaccination employing an attenuated retrovirus having a debilitated transcriptional capability.

BRIEF DESCRIPTION OF THE DRAWINGS

FIGS. 1A and 1B are flow diagrams depicting the preparation of plasmid pCP-envB-R.

FIG. 2 is a flow diagram depicting the preparation of pKC-ΔXho carrying the FeLV-B envelope glycoprotein gene from pKC125.

FIG. 3 illustrates the FeLV-B envelope gene (env) shown with the coding strand in the 5' to 3' direction. The env gene fragment includes a first BalI restriction site between nucleotides 100 and 101 in the leader sequence, and a second BalI restriction site between nucleotides 1519 and 1520 in the p15E region.

FIG. 4 is a flow diagram depicting the preparation of plasmid pCG-envB-R.

FIG. 5 is a schematic of the protocol for modifying the LTRs of FeLV-B.

FIG. 6 is a partial nucleotide sequence homology between FeLV-A, -B and -C.

FIG. 7 is the amino acid sequence homology of the env proteins of FeLV-A, -B and -C.

DESCRIPTION OF THE SPECIFIC EMBODIMENTS

Novel methods and compositions are provided for protecting a mammalian host from viral pathogenic infection under conditions substantially insuring a strong immunogenic response, while minimizing the likelihood of infection from a live vaccine. The method involves the administration of a composition to a mammalian host, which composition comprises at least one envelope protein or immunogenic fragment thereof of the viral pathogen of interest. This envelope composition may be administered one or more times, having the same or modified composition with subsequent administrations. At a reasonable interval, an attenuated mutant of the viral pathogen is administered at a level sufficient to provide immunogenic response. The attenuation is as a result of at least one mutation in the viral pathogen resulting in transcriptional debility. Thus, by virtue of the prior administration of the initial priming function of the envelope composition, in conjunction with the debilitated nature of the attenuated viral pathogen, the host is able to successfully overcome the pathogen by mounting a strong protective immunogenic defense which protects the host from any future invasion by the pathogen.

Enveloped viruses have one or more genes encoding for envelope proteins, which are glycoproteins which occur in a membrane which surrounds the capsid of the virus. In many situations, the immunodominant sites are present on the glycoprotein as the result of epitopic sites involving the polypeptide chain and/or polysaccharide side units. Frequently, the env gene encodes for a precursor to the final envelope protein(s) where the precursor is subsequently processed by cleavage to one or more membrane glycoproteins. For use in the envelope composition, a single intact or mixture of intact envelope proteins may be employed or the fragments of the external portion of the envelope protein(s) or combinations thereof. It will usually not be necessary for the purpose of this invention that the envelope protein include the membrane integrator portion or the cytoplasmic portion.

The envelope proteins may be prepared in a variety of ways. The virus may be grown in an appropriate host and culture, harvested, lysed, and the envelope glycoproteins isolated and purified. Alternatively, the genes may be isolated and manipulated in a variety of ways for providing the intact envelope protein or an immunogenic fragment which will form immune complexes with antibodies induced by the wild-type virus in the mammalian host.

The subject invention finds use with a wide variety of retroviruses which infect mammals, including domestic animals, primates, including humans, and the like. Included among these retroviruses are human T-cell lymphotropic viruses (HTLV-I, -II and -III), feline leukemia virus (FeLV), murine leukemia virus (MuLV), bovine leukemia virus (BLV), feline sarcoma virus (FeSV), murine sarcoma virus (MuSV), simian leukemia virus (SLV), simian sarcoma virus (SSV), avian leukosis virus (ALV), equine infectious anemia virus (EIAV), or the like. These retroviruses, also referred to as oncornaviruses, are the primary focus of the subject invention. Nevertheless, other viruses which share characteristics comparable to the subject viruses, and which may be modified in a manner analogous to the subject viruses, may also find use.

In describing the subject invention, preparation of the envelope composition will be considered first.

The retroviruses will normally have at least three regions, the regions being referred to as the gag, pol and env regions, with the env region being adjacent the right long terminal repeat. (By region is intended the sequence which is required for expression of a product or the maximum response, e.g., enhancer, promoter, etc.) With HTLV-I and -II, the env protein will be a protein referred to as gp41, while with HTLV-III the env protein may be gp130, gp110 or gp41, a fragment of gp110. With FeLV, the env protein is gp70 and will vary depending upon whether group A, group B or group C is involved. For the avian virus, the precursor protein will be gp90 which is cleaved to form gp85 and gp35, joined by a disulfide linkage, and p10. For the murine virus, the precursor gp90 is cleaved to form gp71 joined to p15E by a disulfide linkage and p12E. In each case, the virus may have a variety of serotypes, which differ in their immunogenicity or epitopic sites of one or more the envelope proteins. Thus, the envelope composition may involve one or more serological types or a composite polypeptide chain which mimicks cross-reactive epitopic sites of two or more serological types. Furthermore, a polypeptide chain may be prepared which has differing regions, where each of the regions may provide for one or more epitopic sites to be found in the wild-type serological strain of the retrovirus. Thus, the envelope composition can be varied in a variety of ways to insure that the priming may provide for protection from a single serotype or a group of serotypes, which to some degree will depend upon the nature of the retrovirus which will be subsequently administered.

Thus, the envelope compositions will include at least one polypeptide which is cross-reactive with an epitope of an envelope protein of at least one retro-virus of interest. The polypeptides of the envelope composition may be glycosylated or unglycosylated, may include varying degrees of glycosylation, or may include combinations thereof.

Where other than the wild-type envelope protein is employed, it will usually be necessary to employ hybrid DNA technology to express the polypeptide. Those situations where it will not be required is where the polypeptide has one or more sites recognized by a protease, where the fragments are useful in the envelope composition or where the fragments range from about 15 to 60 amino acids, usually from about 20 to 60 amino acids, and can be synthesized by an automated synthesizer. See, for example, U.S. Pat. No. 4,483,964.

Conveniently, the polypeptides of 30 amino acids or greater will usually be obtained by employing hybrid DNA technology where a nucleotide sequence is employed which codes for the polypeptide of interest.

(Hereinafter, unless specified otherwise, the phrase "envelope gene" intends the DNA sequence coding for at least an immunogenic portion of a retrovirus envelope protein cross-reactive with at least one epitopic site of a retroviral envelope protein.)

In the present invention, an envelope protein gene is obtained and expressed in a suitable microorganism or mammalian cell host. The nucleotide sequence of the gene may be similar or substantially identical to the naturally-occurring sequence from which it was derived, so long as the polypeptide product retains the immunological activity of at least a portion of the natural envelope protein.

For the intact envelope protein or large fragment thereof, the proviral dsDNA form of the retrovirus can be isolated and cloned, although it is also possible to employ cDNA obtained directly from the viral RNA. Proviral DNA is obtained by restriction digestion and gradient fractionation of the genomic DNA from an infected mammalian cell line. Fractions containing fragments of suitable length, usually about 8 to 25 kbp, may be identified and concentrated by ethanol precipitation. These fragments may be cloned in a suitable cloning vector, and recombinant clones carrying the env gene DNA identified using a suitable probe. Such probes may employ RNA obtained from the virus itself, or DNA or RNA obtained from related viruses, such as viruses, which display substantial homology with the subject RNA. Alternatively, the probes may employ synthetic DNA based on the envelope gene sequence, when known.

In addition to the coding sequence for the envelope protein of interest, the DNA constructs of the present invention will include at least a promoter which is recognized by a microorganism host. The microorganism host will usually be yeast, although other microorganism capable of appropriate expression of the gene product will also be suitable.

A wide variety of suitable promoters are available from yeast. Promoters of particular interest include those promoters involved with enzymes in the glycolytic pathway, such as the promoters for alcohol dehydrogenase, glyceraldehyde-3-phosphate dehydrogenase, pyruvate kinase, triose phosphate isomerase, phosphoglucoisomerase, phosphofructokinase, and the like. Particularly preferred are the inducible promoters of glyceraldehyde-3-phosphate dehydrogenase and pyruvate kinase. For example, when yeast cultures are shifted from growth on acetate to glucose, the activity of glyceraldehyde-3-phosphate dehydrogenase is increased up to 200 fold. By isolating these promoters with their naturally-occurring flanking regions including transcriptional regulatory sequences, such as enhancers, operators, etc., and using a host having an intact regulatory system, one can regulate the transcription and expression of the envelope gene by properly controlling the nutrient medium.

The DNA construct will usually include a terminator proximate to the 3'-end of the envelope gene. Conveniently, the terminator can be the terminator which is naturally associated with the promoter. When a different terminator is used, it should be selected to be balanced, i.e., a strong promoter should have a strong terminator and a weak promoter should have a weak terminator. Strong promoters and terminators are preferred since they provide for increased expression of the envelope gene.

To form an extrachromosomal element, the DNA construct will be provided with a replication system capable of providing for stable, extrachromosomal replication in the host of interest. Both bacterial and yeast hosts will be of use, although yeast hosts are preferable for expression. Yeast hosts may allow for post-translational modification, e.g., glycosylation, which may increase the immunological similarity between the polypeptide product of the present invention and naturally-occurring envelope glycoproteins.

A number of suitable yeast replication systems are reported by Botstein et al., *Gene* (1979) 8:17-24. Of particular interest are the YEp plasmids which contain the 2μm plasmid replication system. The 2μm replication system can provide for stable maintenance of multiple copies of the plasmid in yeast. When used for cloning of the DNA construct, the replication system will usually be bacterial. Suitable bacterial replication systems are well known and widely reported in the patent and scientific literature. Often, it will be desirable to employ a shuttle vector having both yeast and prokaryotic replication systems to allow for cloning and expansion of the DNA construct in a prokaryotic host and expression of the product in yeast.

In addition to the envelope gene, promoter, terminator, translation regulatory sequences and replication systems, the DNA construct may be provided with one or more regions which facilitate identification of transformants, regulate replication of the plasmid, or regulate expression of the envelope gene. For example, the DNA construct will usually be provided with markers which allow for selection of transformants. Conveniently, genes may be provided for biocide resistance, such as antibiotic resistance or heavy metal resistance. Alternatively, a gene expressing a particular metabolite will allow for selection of transformants in an auxotrophic host.

Other capabilities may also be introduced into the DNA construct. For example, sequences homologous to a host chromosome may be provided for integration into the host genome. Genes may then be included in the construct which are amplifiable. Upon integration into the genome, genes are amplified in response to stress to the host. By placing such amplifiable genes upstream from the promoter, coding sequence and other signals regulating expression of the envelope gene, and stressing the host, multicopy genes may be obtained with a plurality of tandem repeating sequences capable of expressing the polypeptide(s) of interest. Illustrative amplifiable genes include metallothioneins and dihydrofolate reductase.

Additionally, certain temperature-sensitive regulatory regions allow for modulation of transcription by varying the temperature. Thus, by introducing such a sequence a suitable distance upstream from the promoter, and growing the microorganism host at a "non-permissive" temperature which lessens transcription, one can grow the cells to high density before the expression of the product of interest. After high density has been achieved, the temperature can be adjusted to provide for maximum expression of the polypeptide. Useful temperature-sensitive regulatory regions may be obtained from the genes coding for heat-shock proteins found widely in prokaryotes and eukaryotes.

Often, it will be desirable to join the envelope gene to secretory leader and processing signals to provide for secretion and processing of the envelope protein. Various secretory leaders and processing signal sequences have been described in the scientific and patent literature. See, for example, U.S. Pat. Nos. 4,336,336, 4,338,397 and 4,411,994 as well as copending application Ser. Nos. 522,909, filed Aug. 12, 1983, and 488,857, filed Apr. 26, 1983, the relevant portions of which are incorporated herein by reference.

In preparing the DNA constructs of the present invention, it will usually be necessary to join the various individual DNA sequences described above together in a predetermined order. Since the sequences are derived from diverse sources, it will often be convenient or necessary to join the sequences by means of connecting or adaptor molecules. Such adaptor molecules are short synthetic dsDNA fragments, typically having cohesive ends selected to join to the ends of the DNA sequences derived from natural sources. The nucleotide sequence of the synthetic adaptors can be chosen to regenerate portions of the natural DNA sequences which were excised when the sequences were obtained by restriction from larger fragments. Additionally, the adaptors can be utilized to introduce new restriction sites at desired locations in the DNA construct, and the length of the linking fragment can be selected to assure that the individual DNA sequences are properly spaced apart.

Methodology for manipulating individual DNA constructs is amply described in texts such as Maniatis, et al., "Molecular Cloning" (1982) Cold Spring Harbor Laboratory. Generally, two DNA sequences of interest are joined in vitro using techniques such as homopolymer tailing, annealing of cohesive ends, blunt end ligation, linkers, or the like. By providing selective markers on one or both of the sequences, recombinant molecules combining both sequences in the proper order can be identified. Further screening or scoring using DNA/RNA probes may also find use. After the desired recombinant molecule is identified, the molecule can be cloned in a convenient host, usually prokaryotic, to expand the number of recombinant molecules. Multicopy plasmids, amplifiable genes, and the like, are useful at this stage. After the host carrying the recombinant molecule is grown out, the recombinant molecule may be isolated and used as a source of DNA for the next step in preparing the DNA construct. These manipulations may be repeated as many times as necessary until all the DNA sequences have been joined in the proper order.

In preparing the exemplary DNA constructs described in the Experimental section hereinafter, advantage was taken of preexisting vectors, one of which included the promoter and terminator derived from pyruvate kinase (plasmid pPYK-A) and another of which included the promoter and terminator derived from glyceraldehyde-3-phosphate dehydrogenase (plasmid pUH28). A third preexisting plasmid (pKC125, pFeA12ΔXS or pFeClAΔXS) carrying the entire env gene locus of FeLV (including both gp70 and p15E, see FIG. 3) from FeLV(-B, A or C, respectively) was also utilized. As described in detail in the Experimental section, a portion of the envelope gene encoding the gp70 glycoprotein was inserted between the pyruvate kinase promoter (including a portion of the pyruvate kinase coding sequence) and terminator in pPYK-A, and the resulting fragment carrying the promoter, the FeLV envelope gene including a complete gp70 sequence and partial p15E sequence and terminator, in proper order, was inserted into yeast plasmid pCl/1 to provide pCP-envA, B or C. Similarly, the same FeLV gene sequence as above encoding for gp70 was inserted between the GAPDH promoter and terminator on pUH28, and the resulting fragment carrying the promoter, gp70 gene and terminator, in proper order, was then inserted into plasmid pCl/1 to form pCG-envB.

The plasmids of the present invention may be introduced into the expression host by any convenient means, employing whole cells or spheroplasts, and using polyethylene glycol precipitated DNA for transformation, or liposomes, or other conventional techniques. The modified hosts may be selected based on the genetic markers which are provided. For example, plasmids carrying a gene which complements an auxotrophic host, may be selected based on prototrophy of the auxotrophic host. Alternatively, resistance to a biocide may be selected for by providing the biocide in the culture medium. The cells containing the plasmid may then be grown in an appropriate nutrient medium, and the desired polypeptide isolated using conventional techniques. The desired polypeptide may be purified by chromatography, filtration, extraction, or the like. Conveniently, when the polypeptide is secreted into the medium, the nutrient medium may be recycled by continuously removing the envelope glycoprotein.

After administration of the envelope composition one or more times at appropriate intervals of about one to three weeks, usually not more than about four times, more usually not more than about three times, and preferably one to two times. At an appropriate interval of from one to six weeks, more usually from about one to four weeks, subsequent to the last administration of the envelope composition, the attenuated virus may be administered one or more times, conveniently at the intervals previously indicated.

The attenuated viruses will be attenuated by virtue of a mutation in the long terminal repeats (LTRs) involving transcriptional regulation of the viral genes, where the modification is not compensated for by the other LTR. Thus, the modified virus may be as a result of a natural event, but will normally involve in vitro manipulation to have achieved the desired modification.

With retroviruses, each of the LTRs includes sequences involved in transcriptional regulation. By modifying one or more of the sequences involved in transcriptional regulation, so as to substantially diminish but not destroy transcriptional ability of the viral DNA, either the modified provirus, e.g. as a cloned viral DNA insert, when transfected into a host, or the modified progeny virus, upon infection, e.g. by inoculation, may be employed in the second stage as a vaccine to protect the host against infection from a wild-type virus.

The life cycle of the retrovirus results in a variety of structures. The viral RNA genome has different sequences at the 5'- and 3'-termini referred to as U5 and U3, respectively. Upon reverse transcription into DNA the termini result in the left and right long terminal repeats (1- and r-LTR) which are combinations of U3 and U5 in that order at each terminus. This cellular viral DNA may then become integrated into the host genome to provide the proviral DNA.

Since DNA is more readily manipulated, the two LTR's are modified so as to be non-complementary, rather than directly modifying U3 and/or U5 which would provide the same result. Thus, the virus is attenuated or disarmed by providing at each stage of its life cycle a defective transcriptional regulatory system.

When referring to modification, the modification will preferably include removal of a portion of or all of the enhancer region of the LTR. Generally at least one base will be involved, more usually at least two bases, preferably at least about 5 bases, and more preferably 20 or more bases, and usually not more than 250 bases, more usually not more than 150 bases. The modification results in diminution of the transcriptional activity resulting from the LTR, while substantially diminishing the replication capability of the virus, as well as its pathogenicity. Usually, replication will be diminished under comparable circumstances of growth between the wild-type virus and the modified virus by a factor of at least 2, more usually by a factor of at least about 5.

The modification to the viral DNA may involve a deletion, substitution, inversion, insertion, or the like. The significant factor is that the modification should provide an extremely low, preferably no, possibility of reversion to wild-type and the other LTR must be changed in a manner which inhibits complementarity by such other LTR to restore wild-type transcriptional activity by recombination.

The long terminal redundant or repeat sequences of the oncornaviruses or retroviruses will generally range from about 300 to 1200 base pairs (bp). Illustrative of these long terminal repeats is the LTR of feline leukemia viruses which are about 475–500 bases per strand with the provirus LTRs being 484 for subgroup A, 482 for subgroup B and 488 for subgroup C. The LTRs will normally include within their sequence a number of transcriptional regulatory sequences for initiation, processing etc., such as an RNA polymerase binding site (promoter), enhancer, TATA box, CAAT box, cap sequence, polyadenylation processing signal, and terminator. The enhancer will generally be of about 50 to 100 bp and will usually be found about 100 to 150 bp upstream from the TATA box. The CAAT box will generally be about 50 bp upstream from the TATA box.

The debilitated retrovirus can be provided as a DNA or RNA sequence which retains the genetic functions of the wild-type virus essential for limited replication and infectivity, while being modified so as to have a substantially reduced pathogenicity and rate of replication in a host. This can be achieved by a variety of strategies. An exemplary strategy is to diminish or destroy the enhancer function in one LTR, particularly the right LTR, while also destroying the ability of the left LTR to provide complementary sequenoes to the lost enhancer structure, to prevent restoration of the wild-type enhancer function by recombination.

Diminution of the enhancer function can be achieved by a mutation, inversion, insertion, deletion, or combinations thereof preferably by at least a deletion. Deletions can be conveniently introduced where a restriction endonuolease site is present. This may involve insertion of the viral DNA into a convenient vector for amplification in a suitable host and purification, followed by molecular genetic manipulation of the virus in the LTR region. Desirably, the restriction endonuclease site in the LTR used for genetic manipulation should be unique to the LTR regions, although partial digestions can be employed with lower efficiency. A deletion may then be introduced by treatment with a double-strand-specific exonuclease.

While the left and right LTRs may be treated the same, they may also be treated differently. To that extent, the left and right LTRs may be separated for modification into different plasmids with appropriate flanking regions of the LTRs, so that the two portions of the virus may be subsequently reassembled to restore the viral DNA structure to provide for the reduced replication and infectious function. To avoid complementarity and thus prevent recombination dependent upon DNA sequence homology, the other LTR may be truncated, conveniently from the same restriction endonuclease site at which the above deletion was introduced in the first LTR.

Other mechanisms exist for modifying the LTRs, such as primer repair, which can provide for replication from a particular site in the LTR and loss of the LTR upstream from that site, in vitro mutagenesis, which can provide for deletions, insertions or mutations, use of transposons to provide for deletions, or the like. The particular mechanism used to destroy complementarity of the modified regions in the two modified LTRs present in the cloned provirus, portions of each of which are to serve as a template and be transcribed, replicated and retained in the progeny virus or cellular provirus, may be achieved in different ways.

Experience with the LTRs of one retrovirus can be translated to other retroviruses. For example, the three subgroups of feline leukemia virus and several strains of murine leukemia virus have a high degree of homology in the LTR. The MCF-MuLV has an enhancer region that is 75 bp long, which can be aligned with the enhancer region of FeLV-B, where the 67 bp enhancer segment of the FeLV shares 56 bp with the MCF-MuLV. Thus, a comparison of the regulatory sequences from one retro-virus with those of others can be used for the determination of analogous regulatory sequences in different retroviruses by nucleotide sequencing and the like.

Once the appropriately modified LTR has been manipulated and cloned, the plasmid containing the viral DNA with a modified LTR may be used as a provirus for either transfection of tissue culture host cells and passaging or introduction into an animal via inoculation. From transfected cells showing virus production, which can be determined by any convenient assay, e.g. an assay for reverse transcriptase activity, the viruses may be recovered by any convenient procedure. Alternatively, the virus may be harvested and used for infection of a host and the host bled to produce additional virus and/or antibody.

The subject envelope compositions and attenuated virus compositions can be provided for vaccination of appropriate hosts. Thus, individual vials may be packaged together in predetermined amounts to provide for individual dosages or multiple dosages, where the volume may be in small excess of a multiple of the individual dosages. The ratio of envelope composition to attenuated virus composition in the vials will reflect the number of individual vaccinations to be given to a particular host.

The concentration of the dosage will be sufficient to provide an effective immune response. For the envelope composition, the amount of polypeptide will generally be from about 1 µg to 20 mg/kg host, usually from about 5 µg to 2mg/kg host, although this figure may vary depending on the type of administration, frequency of administration, and the like. The polypeptide may be in any convenient physiologically acceptable medium, for example, sterile water, phosphate buffered saline, growth medium, or the like with or without adjuvant. Usually, the total dosage volume will be about 0.5 to 2.0 ml. Administration may be by injection, either subcutaneously, intramuscularly, intraperitoneally, or the like. Booster injections will be employed as necessary, oral or other convenient means. Immunization with polypeptide from each serological type of the retrovirus may be utilized, or a combination of two or all of them, or the equivalent.

The attenuated virus vaccine will include a sufficient amount of either the modified, cloned proviral DNA or the virus or combination thereof to provide an immune response. The amount of virus will be from about $10^4$ to about $5 \times 10^6$, usually $5 \times 10^5$, focus-forming units/kg host while the amount of viral DNA will be about 50 to 1000 µg DNA/kg host. The viral DNA, provirus or virus may be in any convenient physiologically acceptable medium, e.g. sterile water, PBS, growth medium, or the like. Usually, the dosage volume will be 0.5 to 2 ml.

Administration of the vaccine dose may be by injection subcutaneously, intramuscularly, intraperitoneally, intravenously, or the like, oral administration or other convenient means The following examples are offered by way of illustration and not by way of limitation.

EXPERIMENTAL

Unless otherwise indicated, all percentages are by weight and all temperatures are in Celsius.

The following abbreviations are used:

Amp$^R$—ampicillin resistant
ATP—adenosine triphosphate
CAA—casamino acids
DMSO—dimethyl sulfoxide
DTT—dithiothreitol
LSB—Laemmli protein gel sample buffer
STC—1 M sorbitol, 10 mM CaCl$_2$, 10 mM Tris (pH 7.5)
TE—10 mM Tris 1 mM EDTA
PBS—phosphate saline buffer
PEG—polyethylene glycol
SDS—sodium dodecyl sulphate
tet$^R$—tetracycline resistant
dNTP—dATP, dCTP, dGTP or dTTP

A. GENERAL METHODS

A.1. Restriction Enzymes

The following restriction enzymes were employed in a high salt buffer (10×: 1.5 M NaCl, 100 mM MgCl$_2$, 100 mM Tris, pH 7.5): BamHI, XhoI, XbaI and SalI. EcoRI was employed in a medium salt buffer 10×: 500mM NaCl, 100 mM MgCl$_2$, 100 mM Tris, pH 7.5). BalI was employed in a low salt buffer (10×: 100 mM NaCl, 100 mM MgCl$_2$, 100 mM Tris, pH 7.5). Restriction was accomplished with 2 units of restriction enzyme per µg DNA (25 µl total volume) at 37° C.

A.2. Ligation

One µg DNA in a total volume of 100 µl of buffer (10 mM Tris, pH 7.5, 10 mM MgCl$_2$, 2 mM ATP, 5 mM DTT) and 1 µl T4 ligase (New England Biolabs, approximately 400 units), incubated at 4° C. for 4–6 hr. For blunt end ligations, include 1.5 mM spermidine in the reaction mixture and ligate for a total of 14–24 hr.

A.3. Sequencing

Nucleotide sequencing was performed as described by Sanger and Coulson, *Proc. Nat. Acad. Sci. USA* (1977) 74:5463–5467. Amino acid sequences were determined based on the nucleotide sequences.

A.4. Construction of Plasmids

DNA fragments having cohesive ends were joined by annealing and ligating under the following conditions. One µg DNA in a total volume of 100 µl of buffer (10 mM Tris, pH 7.5, 10 mM MgCl$_2$, 2 mM ATP, 5 mM DTT, 1 μl Biolabs T4 ligase, approximately 400 units), was incubated at 4° C. for 4-6 hrs. DNA fragments having blunt ends were ligated under the same conditions but for 12 to 15 hrs. Recombinant plasmids were cloned as follows. The DNA (about 1 μg) was added to 100 μl of competent *E. coli* HB101 cells (1-2×10$^7$ cells/μl), and the mixture incubated at 4° C. for 20 min., at 37° C. for 2 min., and at room temperature for 15 min. To the mixture was then added 1 ml of L-broth, and the mixture was shaken for 60-90 min. at 37° C., followed by plating on L-agar under selective conditions.

A.5 Klenow Procedure for Restoring and Joining Blunt Ends

A reaction volume of 50 μl of a buffer (6 mM Tris, pH 7.5, 6 mM MgCl$_2$, 1 mM DTT, 50 mM NaCl) and 50 μM each of the four dNTP was incubated at 37° C. for 30 min. in the presence of 5 units of DNA polymerase I, and the reaction stopped by extracting with phenol/chloroform (1:1). For ligation of two blunt ends, the DNA was spun down, the pellet washed one time with ethanol, the pellet resuspended in 8.3 μl of water and 5 μl each of 20×Tris-MgCl$_2$, 20 X ATP, 20 X DTT, and 2 μl 100 mM spermidine added.

A.6. Preparation of Linkers

Linkers were prepared by the method of Beaucage and Caruthers, *Tetrahedron Lett.* (1981) 22:1859-1862.

A.7. Plasmid Amplification and Isolation

One ml of an overnight saturated bacterial culture was added to 100 ml of an amplification medium (20×M9 mix, 5ml; 10×M9 salts, 10 ml; L-broth, 10ml; 1% B1, 0.1 ml; 20% CAA, 0.5 ml; 1% Leu, 1 ml; 1% Pro, 1 ml; 2% Amp/DMSO, 0.2 ml) and cells were grown to O.D.$_{650}$=1 in a 37° C.-airshaker (about 4 hr.). Ten ml L-broth; 0.5 ml 20% CAA and 1 ml of 50% glucose were then added and the cells grown for an additional 30 min. An aliquot of 0.5 ml of a freshly prepared solution of 50 mg/ml chloramphenicol in 100% ethanol was added to the mixture and the culture grown overnight.

The culture was spun down in a 250 ml Beckman centrifuge bottle, 4.5 K rpm/20 min. in a Beckman J-6B. The pellet was suspended in 10 ml of 0.15 M NaCl, 50 mM Tris, pH 7.5 and centrifuged as described before. The pellet was resuspended in 1 ml G.E.T. (25 mM Tris, pH 8, 10 mM EDTA, 50 mM glucose), an additional 1 ml of G.E.T. containing 4 mg/ml of lysozyme was added, and the mixture cooled on ice for 45 min. Four ml of 0.2 N NaOH, 1% SDS, were added followed by gentle mixing and incubating on ice for 15 min. Three ml of 3 M potassium acetate, pH 4.8, were added and after cooling on ice for 1 hr, the mixture was spun at 10 K rpm/20 min. in a Beckman J2-21 (rotor JS-13). The supernatant was diluted with an equal volume of isopropanol. The mixture was allowed to stand at room temperature for 5 min., followed by centrifugation at 10 K rpm/20 min. The resulting pellet was suspended in 1 ml T.E., 5 μl RNAse A (10 mg/ml in 50 mM sodium acetate, pH 4.8; boiled 10 min.) added and the mixture allowed to stand at room temperature for 20 min. One-half volume of 30% PEG 8000/1.5 M NaCl was then added to the mixture and cooled on ice for 30 min., followed by centrifugation at 10 K rpm/20 min. The pellet was redissolved in 0.4 ml T.E., transferred to a 1.5ml microfuge tube and extracted two times with phenol/chloroform followed by one time chloroform. The aqueous phase was split into two 400 μl aliquots in two tubes and 3 volumes ethanol added to each. The alkanolic aqueous phases were mixed at which time a thread-like DNA precipitate occurred. After spinning in a microfuge for 5min., the DNA was ethanol rinsed and dried in a Speedvac. The combined pellets were dissolved in water or TE, normally yielding about 0.3-1.0 mg.

A.8. Yeast Transformation

*Saccharomyces carlsbergensis* strain 2150-2-3, (Mat a, adel, leu2-04, cir°) obtained from Dr. Leland Hartwell, University of Washington, was used for transformation. The yeast cells were grown to an O.D.$_{650}$ of about 1 in non-selective medium (100 ml of cells provides about 0.5 ml of spheroplasts). These cells were pelleted in 150 ml sterile Corex bottles by centrifuging for 5 min. at 3 K, followed by washing the resulting pellet with sterile distilled water and repeating centrifugation. The cells were resuspended in 0.05 vol of original culture in 1 M sorbitol with 15% glycerol, followed by freezing in dry ice-ethanol and storing at −70° C.

Spheroplasts were prepared by resuspending cells in 0.05 vol of the original culture volume using 1 M sorbitol, 50 mM potassium phosphate, pH 7.5 (SP). A 50 μl aliquot was diluted to 1 ml with 0.1% SDS and the initial O.D.$_{650}$ value was determined. The cell suspension was made 1 mM DTT followed by the addition of zymolase (10 mg/ml in SP) to provide a concentration of 0.1 mg/ml. The mixture was incubated at 30° C. with gentle shaking and monitored, with the reaction terminated when the O.D.$_{650}$ value was 10% of the original value (about 20-40 min.). The spheroplast mixture was then centrifuged for 3 min. at 5 K, washed with 1 M sorbitol, centrifuged again, washed once with STC, centrifuged, resuspended and washed again. For transformation, approximately 100 μl of spheroplasts in 1 xSTC and 50 μl of DNA in 1 xSTC were combined and allowed to stand for 5 min. at room temperature, followed by addition of 1 ml 40% PEG4000, and the mixture allowed to stand for 10 min. at room temperature. Cells were pelleted (2.5 Krpm, 10 min.), resuspended in 2.5 ml YEPD-1 M sorbitol and allowed to express for 2 hr. at 30° C. with shaking. Cells were spun (2.5 Krpm, 10 min.) and resuspended in 100-500 μl of 1 M sorbitol. The mixture was then plated in selective top agar (10 ml) onto selective leu- plates.

A.9. Growth and Lysing of Yeast Clones

The yeast clone was inoculated into 2 ml of Leu$^{--}$ minimal media, and the yeast cells allowed to grow at 30° C., with shaking for 24-48 hrs. until saturated. The cells were then pelleted in a microfuge for about 30 sec., the supernatant poured off and the pellet resuspended in 50 μl LSB. After boiling for 5 min., the cellular debris was removed by centrifugation for 1 min. in a microfuge and a 10 μl aliquot was run on an acrylamide gel.

A.10. Preparation of FeLV Virus

The cat cell line LU-1 (AK-D, lung cells, A.T.C.C. accession number CCL 150) chronically infected with FeLV-A, B or C, was grown to about one half confluency in 150 cm$^2$ tissue culture flasks. The culture media (DME-10%FCS) was collected and replaced with fresh media each day for the next three days. At the end of the collection, the cells were trypsinized, plated in new flasks at low density and the collection regime was repeated when the cells reached one half confluency. After about one liter of tissue culture media was collected, the media was clarified by centrifugation at 2,200 g for 20 min and the virus was pelleted by centrifugation at 28,000 g for 12 hours. The pellet was resuspended in 10 mM Tris, 100 mM NaCl, 1 mM EDTA and layered on top of a 15-50% sucrose gradient. The gradient was centrifuged at 40,000 rpm in a SW-41 rotor for 2 hours. The tubes were then removed and the visible virus band was aspirated with a syringe and needle. To confirm that this band corresponded to the virus, infected cells were labeled with $^3$H-uridine and the labeled virus was detected in the gradient by determining radioactivity in each fraction. Virus stocks prepared as described above were stored at 4° C. in the sucrose solution from the gradient.

A.11. Preparation of Anti-FeLV Antibodies

Virus prepared as outlined above was mixed with equal volumes of complete Freunds adjuvant and a stable emulsion was made by repeated passage through a hypodermic needle. Twenty to fifty µg of protein (determined by Coomassie blue binding assay) of each virus preparation was then injected intramuscularly into the hind quarters of rabbits. The rabbits were boosted at three week intervals with 20-50 µg of virus protein emulsified in incomplete Freunds adjuvant with intramuscular injections in the hind quarters. Rabbits were bled one week after each boost and viral antibody titers were determined by an ELISA assay against each purified virus.

A.12. Western Analysis

Transformed yeast cells or FeLV protein controls were electrophoresed on 10% polyacrylamide gels (Laemmli, *Nature* (1970) 277:680) and proteins were subsequently electroblotted onto nitrocellulose filters (Towbin, Staehlin, and Gordon, *Proc. Natl. Acad. Sci. USA* (1979) 76:3450). The filter was preincubated with goat serum and subsequently treated with rabbit anti-FeLV antiserum prepared as previously described (Section 11) or with mouse serum against envelope protein prepared as described in Results (Section 6). The filter was then incubated with a second goat anti-rabbit or goat anti-mouse antibody conjugated with horseradish peroxidase (Boehringer-Mannheim) and finally incubated with horseradish peroxide color development reagent (Bio-Rad) and washed.

A.13. Reverse Transcriptase Assay

See Rosenberg and Haseltine, *Virology* (1980) 102:240-244.

B. PREPARATION OF FeLV ENVELOPE COMPOSITION

B.1. Plasmids used in the construction of yeast expression vectors for envelope protein of FeLV-A, FeLV-B or FeLV-C a) Plasmids containing DNA coding for the envelope protein of FeLV-A, FeLV-B or FeLV-C i) Plasmid pKC125 (FIG. 2)

The DNA sequence coding for the envelope protein of FeLV-B was obtained from plasmid pKC125 (obtained from Dr. James Casey, Louisiana State University). This plasmid was obtained by subcloning a 10 Kb EcoRI fragment containing the complete genome of FeLV-B into a 2.2 kb pBR322 derivative which has deletion comprising the tet$^R$ gene. The EcoRI fragment was obtained from a clone λHF60 from a lambda library constructed as described in Mullins et al., *J. of Virol.* (1981) 38:688-703.

ii) Plasmid pFeA12ΔXS

This plasmid was derived from pFeA12A (described below) and contains part of the FeLV-A provirus including all the coding region for the envelope protein. To construct pFeA12ΔXS, a XhoI (site in the provirus sequence)—SalI (site in the vector sequence) deletion was made. To obtain this deletion pFeA12A was digested with XhoI and with SalI. The plasmid was self-ligated and cloned in HB101 to produce pFeA12ΔXS.

iii) Plasmid pFeC1AΔXS

This plasmid was derived from pFeC1A (described below) and contains part of the FeLV-C provirus including all the coding region for the envelope protein. To construct pFeClAAXS, plasmid pFeClA was digested with XhoI and SalI. The plasmid was self-ligated to produce pFeClAΔXS.

iv) Plasmids ΔFeA12A and pFeClA were constructed as follows (see copending application, Ser. No. 593,339, filed 3/26/84)

High molecular weight whole cell DNA from the human RD-4 cell lines infected with FeLV-A or FeLV-C was prepared by phenol-chloroform extraction and a sample of each digested with various restriction endonucleases. The restricted DNA was analyzed by Southern blotting with a$^{32}$P-radiolabeled probe specific to FeLV sequences corresponding to a BssHI fragment of FeLV-B DNA which comprises almost the entire proviral genome since this enzyme cleaves twice in each LTR only. EcoRI restrictions sites were not detected in the proviral DNA in either cell line; therefore, the whole cell DNA preparations isolated from each were digested to completion with EcoRI, centrifuged in sucrose gradients and fractions corresponding to 8-15kb were pooled, dialyzed and concentrated by ethanol precipitation. The bacteriophage derivative cloning vector, EMBL-4 (see Karn et al., *Methods Enzymol.* (1983) 101:3-19) was digested to completion with a mixture of EcoRI, BamHI and SalI restriction enzymes and the DNA then deproteinized by phenol-chloroform extraction, precipitated with cold ethanol and resuspended in ligation buffer. (The brief alcohol precipitation selectively recovers large DNA fragments (e.g., phage arms) while the small linker DNA is retained in solution; SalI/SalI filler fragments are not incorporated into the construct during subsequent ligation.) The EMBL-4 phage DNA and EcoRI digest of cellular DNA are mixed and ligated, and the resultant recombinant phage genomes packaged in vitro. After phage infection of λ-sensitive *E. coli,* phage plaques were transferred to nitrocellulose filters, DNA was fixed and the filters were screened with FeLV-specific radiolabeled probe as above. Positive plaques, consisting of phage containing the entire FeLV-A or C proviral DNAs, together with flanking human (RD-4 cell) DNA, were recovered. Plasmid pFeA12A or pFeClA were then obtained by subcloning the provirus FeLV-A or FeLV-C respectively, from EMBL-4 into pBR328. FeLV-A provirus was inserted into the SstI/EcoRI site of the cam$^R$ gene with resulting plasmid being cam$^S$, amp$^R$, and tet$^R$. FeLV-C provirus was inserted into the EcoRI site of the cam$^R$ gene with the resulting plasmid being cam$^S$, amp$^R$ and tet$^R$.

b) Plasmids containing glyceraldehyde-3-dehydrogenase (GAPDH) or pyruvate kinase (PYK) promoter and terminator sequences.

i) Plasmid pUH28 (FIG. 4)

Plasmid pUH28 contains the coding and 3' noncoding regions of the Hepatitis B surface antigen (HBsAg) gene fused in incorrect reading frame to the first 7 codons of the yeast GAPDH structural gene. This fusion is flanked at its 5' end by the GAPDH promoter and its 3' end by part of the GAPDH coding region followed by the GAPDH terminator. This plasmid was constructed so as to have an NcoI site at the 3' end of the first 7 codons of the GAPDH gene with the following sequence:

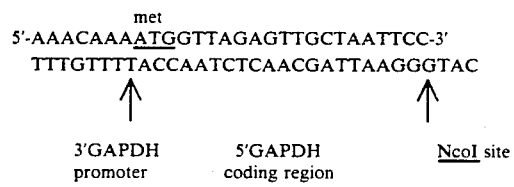

```
              met
5'-AAACAAAATGGTTAGAGTTGCTAATTCC-3'
   TTTGTTTTACCAATCTCAACGATTAAGGGTAC
           ↑              ↑
      3'GAPDH        5'GAPDH         NcoI site
      promoter       coding region
```

The SalI site used in the preparation of the yeast vector containing FeLV sequences is at the 5' region of the GAPDH terminator. Therefore, by digesting pUH28 with NcoI and partially with SalI a deletion of the HBsAg coding plus non-coding regions and of the GAPDH coding region is obtained.

The construction of pUH28 involves cloning of a fragment that contains the HBsAg coding and 607 bp of 3' non-coding region prepared from pHBS5-3 Hae2-1 (described below) into the GAPDH containing vector pGAP$_2$' (described below). To prepare the fragment, pHBS5-3 Hae2-1 was linearized by PstI digestion, partially digested with NcoI and a PstI-NcoI fragment of 1.9 Kb containing pBR322 sequences, HBsAg coding and 3' sequences was purified by gel electrophoresis. This fragment was subsequently digested with EcoRI and a 1.2 Kb NcoI-EcoRI fragment containing the HBsAg coding and 3' non-coding regions was purified by gel electrophoresis. Plasmid pGAP$_2$' was linearized with XbaI and treated with Bal31 to remove approximately 100 bp total. The plasmid was subsequently digested with NcoI and a vector fragment of about 8 Kb was purified by gel electrophoresis. The NcoI ends of the vector and the 1.2 Kb NcoI-EcoRI fragment encoding HBsAg were ligated. The recessed ends were filled in with Klenow and the resulting blunt ends were ligated to the blunt end of the vector obtained by Bal31 digestion to produce pUH28.

pHBS5-3 Hae2-1 is a plasmid that contains the HBsAg coding region and 607 bp of the 3' flanking sequence. This plasmid is a derivative of pHBS5-3 which contains the same insert but only 128 bp of 3' untranslated region instead of 607 bp. Plasmid pHBS5-3 has been previously described in copending application Ser. No. 609,540, filed May 11, 1984 (pp. 13-14). pHBS5-3 Hae2-1 was constructed as follows. The HBV genome (3.2 kb) was excised from pHB-3200 (Valenzuela et al., Nature (1979) 280:815-819) by restriction digestion with EcoRI. The 3.2 kb fragment was purified by gel electrophoresis and was recircularized by ligation of the EcoRI sticky ends. This cloned HBV genome was digested with HaeII, which cuts in the 3' non-coding region. Recessed ends were filled in with Klenow and HindIII linkers were ligated. The DNA was cut with HindIII and subsequently with XbaI, which has a single site in the HBV coding region. A 1.2 kb XbaI-HindIII fragment containing 586 base pairs of the coding sequence of HBV and 607 base pairs of the 3' non-coding region was isolated by gel electrophoresis. This fragment was cloned into pHBS5-3 previously cut with XbaI and HindIII and treated with alkaline phosphatase, to yield pHBS5-Hae2-1.

pGAP-2 is a pBR322 derived vector which contains a BamHI insert that has the GAP coding sequence, 5' and 3' flanking regions. There are two XbaI sites in this plasmid: one in the coding region and one in the 3' flanking sequences. pGAP$_2$' is a derivative of pGAP-2 in which the XbaI site present in the 3' flanking region has been eliminated. For this purpose, 50 µg of pGAP-2 were partially digested with XbaI, treated with Bal31 to remove 25 base pairs per end and ligated. The plasmids were used to transform HB101 and the transformants were selected for loss of the XbaI site in the 3' flanking region.

ii) Plasmid pPYK-A (FIG. 1A)

This plasmid derived from pBR327, contains a 2.89 kb BamHI-ThaI fragment corresponding to the yeast PYK gene. The sequence of this DNA has been described by Burke et al., *J. Biol. Chem.* (1983) 258:2193-2201, and shown to contain 915 bp of promoter sequence, 470 bp of terminator sequences and the whole coding region. This fragment supplied by Burke was ligated to BamHI linkers, digested with BamHI and ligated to BamHI digested pBR327 to produce pPYK-A.

c) Other plasmids used in the construction of yeast expression vectors

The two plasmids described below were used only as a construction vehicle in the preparation of yeast expression vectors since they had convenient restriction sites.

i) Plasmid pAV-4 (FIG. 4)

This plasmid is derived from pAV-1/TK-A (Luciw et al., Cell (1983) 33:705-716) which contains two long terminal repeat (LTR) sequences of Raus Sarcoma virus (RSV), the thymidine kinase gene of Herpes Simplex virus and pBR322 sequences containing the amp$^R$ gene. pAV-1/TK-A was digested with BamHI, diluted and self-ligated. After cloning in *E. coli* HB101 and selecting transformants with ampicillin, plasmid pAV-1 was obtained which had a deletion of the thymidine kinase gene. pAV-1 was subsequently digested with EcoRI. The recessed ends were filled in with Klenow and BamHI linkers were ligated to the blunt ends. After BamHI digestion, the plasmid was recircularized, cloned in HB101 and transformants were selected for amp$^R$. Plasmid pAV-4 which contains only U3 of the RSV-LTR sequences was thus obtained.

ii) Plasmid pMV2ZRI (FIG. 1A)

This plasmid derived from pBR328 lacks EcoRI sites and contains two LTR from Harvey murine sarcoma virus (HaMSV). Preparation of pMV2ZRI was as follows. A 2.3 Kb HindIII-BamHI fragment from clone H-1 (Willumsen et al., *J. Virol.*, (1984) 601-603) was cloned in HindIII-BamHI digested pBR328 to produce pV15-3LTR. This plasmid was digested with XbaI, which cuts once in the LTR sequence, and recircularized. After transformation of *E. coli* HB101 and selection of transformants with ampicillin, pV15-1LTR was obtained in which 2 LTR sequences have been deleted. After BamHI digestion of pV15-1LTR, the recessed ends were filled in with reverse transcriptase, the plasmid was recircularized and used to transform *E. coli* HB101. After selections of transformants with ampicillin, plasmid pV15-(Z-Bam) was obtained. This plasmid was digested with BalI, which cuts once in the insert (outside the LTR sequence) and once in pBR328, BamHI linkers were ligated to the blunt ends and the plasmid was recircularized and cloned in *E. coli* HB101 to produce pV15(Bal→H3). Plasmid pMV-2 was then prepared by joining three fragments: an EcoRI-HindIII vector fragment from pV15(Bal-H3) containing pBR328 sequences and one LTR sequence from HaMSV; a 346 bp HindIII-BamHI from pBR322; and a BamHI-EcoRI fragment from pV15-1LTR containing one LTR sequence from HaMSV. After ligation, the mixture was cloned in *E. coli* HB101 and selection of transformants was carried out with ampicillin. Plasmid pMV2 was digested with EcoRI, the recessed ends were filled in with Klenow and the plasmid was recircularized and cloned in HB101 to produce pMV2ZRI which lacks EcoRI sites.

B.2. Sequences and Features of the FeLV Envelope Genes

The envelope gene of feline leukemia virus is located on the 3′-portion of the viral genome. Sequencing of the envelope gene region (including the leader sequence, gp70 and partial p15E) for each subgroup of FeLV was performed, and the results are presented in Appendix A. Asterisks indicate homology between corresponding bases in the sequence of each subgroup. Sequencing was carried out from the HindIII site located immediately to the right of the center of the viral genome in the pol region. For each subgroup, over 2.5 kbp of continuous sequence was determined. Significant homology was found among the three subgroups, as well as between the subgroups and several strains of murine leukemia virus (MuLV). The similarity to MuLV helped in identifying various functional regions in the FeLV genome. The translational initiation codon (ATG) for all three subgroups is indicated on the sequence in FIG. 6. Coding for the N-terminus of the gp70 envelope protein begins at a location 99 base pairs downstream from the initiation codon. All three subgroups have nearly identical leader peptides. The coding for the p15E envelope protein begins at a location 1350 base pairs downstream from the initiation codon in FeLV-B. For FeLV-C, the distance is 1281 base pairs, and for FeLV-A, the distance is 1290 base pairs.

The amino acid sequences for the envelope proteins from each viral subtype were determined and are set forth in FIG. 7.

B.3. Preparation of pCP-envB-R or pCP-envA-R

A yeast expression vector derived from pCl/1 and carrying the FeLV-B gp70 gene and a portion of the p15E coding region was prepared as illustrated in FIGS. 1A-1B. The pyruvate kinase (PYK) promoter and terminator regions were obtained from plasmid pPYK-A (described under Materials and Methods, section 1.b.). Plasmid pPYK-A was completely digested with restriction enzymes XbaI and SalI and gel purified to separate the resulting two fragments. The longer fragment carrying the Amp$^R$ gene was retained for use later, as will be described below. The shorter fragment carrying the pyruvate kinase gene (with the exception of the first four bases of the coding region) and terminator was inserted into a SalI/XbaI cut on plasmid pMV2ZRI (described under Materials and Methods, section 1.c.. Plasmid pMV2ZRI is free of EcoRI sites.

The resulting plasmid (pMV-PYK) included a single EcoRI site located 32 codons upstream of the termination codon of the pyruvate kinase gene. Plasmid pMV-PYK was digested with XbaI and EcoRI to remove most of the PYK coding region, and after gel purification, a linker was ligated in the resulting XbaI/EcoRI cut. The linker included cohesive ends for XbaI and EcoRI and provided a BalI restriction site (see FIG. 1A). The resulting plasmid (pMP-Linker) was completely digested with XbaI and SalI, and the shorter fragment carrying the BalI restriction site ligated to the larger XbaI/SalI fragment of plasmid pPYK-A obtained earlier. The resulting plasmid (pPYK-Linker) was identical to pPYK-A except that most of the pyruvate kinase gene had been removed and replaced by the synthetic linker which provides for a unique BalI site.

A portion of the FeLV-B envelope gene region (env) was derived from plasmid pKC125. Plasmid pKC125 (described in Materials and Methods, section 1.a.) carries the entire FeLV-B genome. This plasmid was digested with restriction enzyme XhoI to remove the gag and pol genes (FIG. 2). The resulting plasmid (pKC-ΔXho) thus carried the envelope gene region together with a pair of BalI restriction sites at locations near either end. See FIG. 3. The BalI site near the 5′-end cleaves between nucleotides 102 and 103 in the leader sequence. The BalI site near the 3′-end cleaves within the p15E gene, leaving the gp70 envelope protein gene intact.

Referring now to FIG. 1B, the BalI fragment carrying the gp70 gene was excised from pKC-ΔXho and inserted into the unique BalI site on pPYK-Linker, resulting in plasmid pPL-envB. Insertion of the BalI fragment provides a fusion in the correct reading frame with the codons left from the PYK gene and from the XbaI-EcoRI linker (described previously). Therefore, 4 extra codons are fused at the 5′ end of the gp70 gene in the leader sequence region (to nucleotide 103) and 33 codons are fused at the 3′ end of the BalI fragment in the p15E coding region. Plasmid pPL-envB was digested with BamHI to excise the fragment carrying the portion of the envelope gene under transcriptional control of the PYK promoter and terminator regions. The BamHI fragment was then inserted into the unique BamHI restriction site in yeast plasmid pCl/1, and the resulting plasmid (pCP-envB-R) selected based on loss of tetracycline resistance.

A procedure similar to that described above and depicted in FIG. 1B was followed for the construction of pCP-envA-R, a yeast expression vector for the envelope protein of FeLV-A. In this case, plasmid pFeA12ΔXS (described in Materials and Methods, Section 1.a.) was used, instead of pKC-ΔXho, to provide for the FeLV-A env gene.

B.4. Preparation of Plasmid pCG-envB-R (FIG. 4)

A second yeast expression vector was derived from plasmid pUH28 (described under Materials and Methods, Section 1.b.) carrying the HBsAg gene under the transcriptional control of the GAPDH promoter and terminator regions. Plasmid pUH28 was restricted with BamHI and the fragment carrying the promoter, terminator and HBsAg gene was isolated. The BamHI fragment was then inserted into the unique BamHI site on plasmid pAV-4 (described in Materials and Methods, Section 1.c), which plasmid was free from NcoI and SalI sites. After cloning the resulting plasmid (pUH2-8/AV4-B) in *E. coli* HB101, the major portion of the HBsAg gene was removed by digestion with NcoI and SalI.

A BalI fragment from pKC-ΔXho was obtained as described previously in reference to FIG. 2. The BalI fragment was then inserted into the NcoI/SalI cut in pUH28/AV4-P by the Klenow procedure described in Materials and Methods. Inserting the BalI fragment restores the SalI site on the resulting plasmid (pUAB-envB), and also restores a correct reading frame with the first 7 codons of the GAPDH 5'- coding region from pUH28. The NcoI/BalI junction was sequenced to verify the correct reading frame. After expansion in *E. coli* HB101, plasmid pUAB-envB was restricted with BamHI and the fragment carrying the GAPDH promoter and terminator and envelope gene was isolated. The BamHI fragment was then inserted into the unique BamHI site on plasmid pCl/1 to produce plasmid pCG-envB-R.

B.5. Expression in Yeast

Yeast was transformed with pCP-envA-R, pCP-envB-R or pCG-envB-R, as described in Materials and Methods. Transformed yeast were estimated to produce about 2–5% of an approximately 55 kdal polypeptide corresponding to the FeLV-A or FeLV-B envelope protein, based on the total yeast protein produced with both yeast vectors. These estimates were based on Coomassie blue staining of total yeast proteins separated on polyacrylamide gels.

A Western Blot analysis with antibodies (rabbit) specific to FeLV-A or FeLV-B viral particles was performed, as described in Materials and Methods. The analysis identified the expected approximately 55 kilodalton polypeptide, as well as an approximately 30 kilodalton polypeptide. Thus, it appears that some proteolysis of the 55 kilodalton protein occurs in the yeast. Preparation of extracts in the presence of protease inhibitors alleviated the degradation.

B 6. Purification of Envelope Protein from FeLV-A or FeLV-B Synthesized in Yeast Yeast cells transformed with vectors pCP-envA-R, pCP-envB-R or pCG-envB-R were grown to an O.D. $_{650}$=3. Cells were harvested (3K rpm, 10 min.), resuspended in an equal volume of 0.1 M Tris-S04, pH 9.4, 10mM DTT and incubated at 30° C. for 20 min. Cells were pelleted (3 K rpm, 10 min.), resuspended in 5 volumes of 1M sorbitol, 50 mM potassium phosphate buffer pH 7.5 and 0.01 volume of zymolyase (10 mg/ml) were added. The mixture was incubated and monitored with the reaction terminated when the O.D.$_{650}$ value was 10% of the original value (about 30 to 40 min.). The spheroplasts were centrifuged at 3K rpm for 10 min. and washed with 5 volumes of 1M sorbitol. This step was repeated. The final pellet was resuspended in 1 volume of 10 mM Tris (pH 8.0), 10 mM NaCl, 1 mM phenylmethylsulfonylfluoride (PMSF), 1 μg/ml pepstatin and incubated for 5 minutes on ice to provide lysis. The mixture was transferred to microfuge tubes and centrifuged for 15 minutes. The pellet was resuspended in an equal volume of 0.2% SDS, 1 mM PMSF, 1 μg/ml pepstatin. The mixture was incubated 10–12 hours at 4° C. and centrifuged for 15 minutes in the microfuge. The pellet obtained corresponds to approximately 70% pure envelope protein.

For large scale preparations (over 25 ml of packed cells of starting material) volumes are scaled up accordingly. Spheroplasting usually takes 1½–2 hours.

C. PREPARATION OF FeLV ATTENUATED VIRUS

C.1. Preparation of Modified FeLV-B ipRF1,2 and 3×)

A schematic of the protocol for this modification is set forth in FIG. 5.

In order to prepare the modified FeLV-B, pKC125 (obtained from Dr. James Casey, Louisiana State University) was employed, where an 11 kb EcoRI fragment containing the complete genome of FeLV-B, with single copies of the left and right-LTR was inserted into the EcoRI site of pBR328. The plasmid has an ampicillin resistance gene. The plasmid was used in two ways: (1) to provide the right-LTR (r-LTR) with deletions at the EcoRV site; and (2) to provide a truncated left-LTR (l-LTR), from which all the sequences upstream from the EcoRV site had been removed.

(1) An approximately 11kb EcoRI fragment from pKC125 was inserted into the EcoRI site of pBR328 to provide two plasmids having different orientations of the EcoRI fragment, p3B having the orientation from right- to left-LTR in the opposite direction of the orientation of the ampicillin resistance gene, while p25A had the orientation from right- to left-LTR in the same direction as the orientation of the ampicillin resistance gene, with the l-LTR proximal to the 5'-end of the amp$^R$ gene. p3B was used for introducing deletions into the r-LTR. To isolate the r-LTR and to remove all EcoRV sites in the plasmid except the one in the LTR, p3B was digested with a mixture of XhoI and BamHI. The resulting 4bp 5'-overhanging ends were filled in with reverse transcriptase or the klenow fragment of DNA polymerase I. These molecules were circularized with T4 DNA ligase and cloned to provide p3BΔ, where the recircularization restores the XhoI site. The resulting plasmid is ampicillin resistant and tetracycline-sensitive, as compared to the precursor plasmid which is ampR and tet$^R$. p3bΔ was then digested with EcoRV and resected with Bal31 for different periods of time to provide deletions ranging from something under 50bp to a plasmid having a deletion of about 125–150 bp. These three deletions will be referred to as 1, 2 or 3, ranging from the smallest to the largest deletion in that order. Sequencing showed 1 to have a 22 bp deletion at position —234 to —212; 2, a 57bp deletion at —251 to —194; and 3, a 132bp deletion at —286 to —154, where the first base of the r-LTR is defined as —338. The resulting plasmids had a HindIII-XhoI fragment which included the r-LTR with the different deletions and extended through the env gene.

(2) In order to avoid recombination resulting in a wild-type LTR, the l-LTR was now modified. p25A was completely digested with BglII and BamHI which resulted in two fragments, one fragment having the l-LTR, the amp$^R$ gene and an inactivated tet gene. This DNA was circularized with T4 DNA ligase, transformed into *E coli*, recovered by selection for amp$^R$ and tet$^S$ and designated p25AΔ. p25AΔ was then digested with PvuII and EcoRV to provide a fragment where the 1-LTR was reduced in size by removing U3-LTR sequences upstream from the EcoRV site. This fragment was joined by ligation with T4 DNA ligase to a PvuII/EcoRV fragment isolated from pBR328, which fragment had an intact chloramphenicol gene. The resulting plasmid p25AΔcam was cam$^R$, amp$^R$ and tet$^S$. The 1-LTR now lacks a portion of the enhancer region.

p25AΔcam was totally digested with SalI, the overhang filled in using the Klenow DNA polymerase I fragment, followed by complete digestion with XhoI. p3BΔ was totally digested with XhoI and PvuII to provide a fragment containing an intact r-LTR and the env gene. The two fragments were joined to provide plasmid RFW which was cam$^R$ and amp$^R$ and included the partial 1-LTR.

In order to delete a HindIII site adjacent the partial 1-LTR, plasmid RFW was digested with ClaI, resected with Bal31 and ligated to provide plasmid RFWdH3, which lacked the HindIII site adjacent the partial 1-LTR. Plasmid RFWdH3 was then completely digested with XhoI and HindIII, and gel purified. The plasmids p3BΔ1, 2 and 3 and the fragments containing the r-LTR with the different deletions were isolated. The fragments from p3BΔ1, 2 and 3 were each combined with the fragment from plasmid RFWdH3 to provide plasmids F1, 2 or 3, which were cam$^R$, amp$^R$ and included the partial 1-LTR, the deleted r-LTR and the env gene.

The bacterial neo$^R$ gene was excised from pNeo (Bethesda Research Laboratories, Gaithersburg, Md.) as a HindIII/EcoRI fragment and cloned into the HindIII/EcoRI digested, SV40 expression vector plasmid, pSVgt1 (available from Dr. Paul Berg, Stanford University) for use as a selectable marker in tissue culture cells (Southern and Berg, *J. Mol. Applied Genet.* (1982) 1:327-341). This plasmid contains convenient BamHI restriction sites flanking the neo$^R$ gene allowing its excision as a Bam fragment.

In order to restore the other structural genes necessary for infectivity, the plasmid pKC125 was completely digested with BamHI and the Bam fragment having the neomycin resistance gene inserted into the Bam site. This plasmid KC-neo was completely digested with XhoI and a fragment isolated by gel electrophoresis which included the gag and pol FeLV-B genes and the neo$^R$ gene. This Xho fragment was then inserted into the Xho site of plasmids RF1, 2 or 3 to provide plasmids RF(1, 2 or 3)XN, where the FeLV-B virus had the neo$^R$ gene on a BamHI fragment inserted between the pol and env genes while having the modified LTRs in their proper orientation. The subject plasmids were selected on cam/neo plates. The neo$^R$ gene was then removed by BamHI digestion and selection for cam$^R$ neo$^S$ to provide plasmids RF(1, 2 or 3)X, which now had the reconstructed virus with a partial 1-LTR and r-LTR containing the previously indicated deletions.

In order to provide a comparison, a plasmid was constructed having FeLV-B virus with a partial 1-LTR and an intact r-LTR. This construction was derived from the plasmid RFW by digestion with XhoI and combining and ligating with the XhoI fragment from plasmid KC-neo, which contains the gag and pol genes, as well as the neo$^R$ gene on a BamHI fragment. The resulting (RFWXN) plasmid was selected on cam/neo plates, followed by digestion with BamHI to remove the neo$^R$ gene to provide plasmid RFWX, which has an intact FeLV virus except for the partial 1-LTR.

C.2. Cells and Tissue Culture

The following cell lines were employed with their source or reference being indicated Lu-1 (cat, AK-D) and Tg (cat, Fc3Tg) (A.T.C.C.); RD-4 (human), D-17 (dog) and Cos-1 (monkey) cell lines (Tissue culture facility at U.C.S.F.). Cells were propagated in Dulbecco's modified Eagles Medium with 10% fetal calf serum (FCS). Cell cultures were incubated at 37° C., in 95% air, 5% $CO_2$.

For passaging cells were removed from tissue culture dishes by treating the monolayer with a small volume of 0.25% trypsin in STV (saline/trypsin/versene) for 5–10min at room temperature. Cell stacks were frozen at −85° C. in 50% FCS, 10% DMSO growth medium. STV is (per liter of double-distilled water): 8.00 g NaCl, 0.4 g KCl, 1.00 g glucose, 0.58 g NaHCO$_3$, 2.5 g trypsin (Difco 1:250), 0.2 g versene (EDTA) (Gibco), 0.0045 g phenol red; pH adjusted to 7.0–7.1 and sterile-filtered before use.

Two RD-4 cell lines, one infected with FeLV-A/Glasgow-1 and the other with FeLV-C/Sarma strains were obtained from Dr. James Casey of Louisiana State University.

C.3 Cocultivation to Rescue Virus $2 \times 10^6$ Cos-1 cells harboring FeLV-A proviruses were mixed with $2 \times 10^6$ Lu-1 cat cells and seeded in 100 mm tissue culture dishes in growth medium. After reaching confluency in 5 days, the monolayers were resuspended in 0.25% trypsin-STV and $5 \times 10^6$ cells were seeded in fresh medium in 100 mm plates and allowed to reach confluency. After 5 days the cells were passaged once more, grown for 5 days, and the medium was then harvested. This medium was used to infect fresh Lu-1 cells and growth of virus was determined by the reverse transcriptase assay. If the culture were positive, virus was harvested and frozen at −85° C.

C.4. Virus Infection of Tissue Culture Cells

One ml of medium (virus harvest) to be tested for virus was added to a 60 mm dish containing 500,000 cells in 4 ml of growth medium. After 6 hr at 37° C. in an incubator (95% air, 5% $CO_2$) the medium was replaced with fresh growth medium and the dishes returned to the tissue culture incubator. Infected cells were passaged at approximately 5 day intervals. For each passage, cells were diluted 1:10 and seeded in new dishes with fresh medium.

C.5. Virus Harvests

Infected cells were grown on tissue culture dishes until they approached about 80% saturation (as judged by visual inspection with a microscope). Fresh growth medium was applied and cells were incubated at 37° C. for 12 hr. This medium was collected and filtered through a 0.22 μ filter to remove cells and cell debris. In some cases, a large amount of medium was collected and centrifuged at 5,000 rpm for 10 min at 4° C. to pellet cells and cell debris (clarified virus). The supernate was transferred to a 36 ml polyallomer tube and centrifuged in an ultracentrifuge at 25,000 rpm for 1 hr at 4° C. in a SW28 rotor. The supernate was decanted and the pellet (containing virus) was resuspended in 1 ml of growth medium. Medium from uninfected cells was similarly prepared for mock-infected controls.

C.6. DNA Transfection

Co-precipitates of DNA and calcium were prepared according to modifications of the method of Graham and Van der Eb, *Virology* (1973) 52:456. The co-precipitates were made in Hepes buffered saline (HBS; 16 g NaCl, 0.74 g KCl, 0.39 g $Na_2HPO_4.7H_2O$, 1 g dextrose, 5 g Hepes, pH adjusted to 7.05). A total mass of 20 μg of DNA (composed of 18 μg of salmon sperm carrier DNA and 2 μg of FeLV-plasmid DNA) was dissolved in 0.5 ml of 250 mM $CaCl_2$. To this solution was added dropwise, 0.5 ml of HBS and the solution mixed by bubbling a stream of air. To one dish (60 mm) of 500,000 cells in 5 ml growth medium was added 0.5 ml of the co-precipitate. The dishes were incubated 6 hr at 37° C. (95% air, 5% $CO_2$); the medium was then removed by aspiration, and the cell monolayers were treated for 4 min at room temperature with 1 ml of a 15% glycerol solution in HBS. The glycerol solution was then replaced with 5 ml of growth medium and the monolayers placed in a cell incubator. After 4-5 days, the cells were passaged by diluting cells from the confluent dish 1:10 in a new dish with fresh medium. The cells were similarly passaged 3 additional times, and the medium was assayed for reverse transcriptase activity.

C.7 Recovery and Characterization of Infectious Viruses from Plasmids Containing Proviruses To recover infectious viruses, the reconstructed plasmids were transfected into several lines of tissue culture cells permissive for FeLV-B. After approximately 4 weeks of serial propagation, each transfected culture was tested for virus production by assaying for reverse transcriptase activity of the tissue culture medium. All cultures transfected with plasmids containing the FeLV-B proviruses, RFWX, RF1X, RF2X and RF3X were positive. A control culture that received pBR328 DNA was negative.

Virus was harvested by collecting medium, which was used to infect fresh lines of permissive cells. These infected cells were serially passaged for four weeks, ensuring that every cell in each culture was infected. To verify the structure of proviral DNA, high molecular weight DNA was prepared from the infected cell cultures by phenol-chloroform extraction, digested with restriction endonucleases and analyzed by the Southern blotting procedure. For hybridization, radio-labeled DNA probes representative of the FeLV-B provirus were prepared. Digestion with a mixture of KpnI and SacII of DNA from cells infected with wild-type virus (derived from proviral plasmid RFWX) showed the expected pattern, including a 1.0kb DNA fragment that encompasses the U3 portion of the wild-type virus LTR. Cells infected with virus derived from proviral plasmid RF3X share the same DNA fragments except that the 1 kb DNA fragment is absent; instead, a new 0.9kb DNA fragment is observed. Digestion of the cellular DNA samples with EcoRV shows that wild-type (RFWX-derived) cellular provirus has EcoRV sites in both LTRs, whereas the ΔRV3 (RF3X-derived) cellular provirus has only the internal EcoRV sites and no EcoRV sites in either LTR. Thus, the integrated cellular provirus recovered from the reconstructed RF3X proviral plasmid and by inference the viral RNA genome retain the deletion in the LTR or LTR-derived region (U3), respectively.

The recovered viruses were used to infect a variety of tissue culture cells and replication was measured by assaying for virion-associated reverse transcriptase in the growth medium. The following Table 1 shows that the viruses containing the deletions grow less well than wild-type virus.

TABLE 1

| Virus replication in tissue culture cells measured by virion reverse transcriptase activity. | | | | |
|---|---|---|---|---|
| | reverse transcriptase activity ($\times 10^3$) virus strain | | | |
| Cell line | RFWX | RF1X | RF2X | RF3X |
| Cat (Lu-1) | 53 | 23 | 28 | 16 |
| Dog (D17) | 24 | 4 | 7 | 2.2 |
| Human (RD4) | 34 | 17 | 13 | 8 |

C.8. Cloning of FeLV-A and FeLV-C Proviruses with Enhancer Deletions

High molecular weight whole cell DNA from the human RD-4 cell lines infected with FeLV-A and FeLV-C (vide supra) was prepared by phenol-chloroform extraction and a sample of each digested with various restriction endonucleases and analyzed by Southern blotting with a $^{32}P$-radiolabeled probe specific to FeLV sequences: the BssHII fragment of FeLV-B DNA (pRFWX) which comprises almost the entire proviral genome since this enzyme cleaves twice in each LTR only. EcoRI restriction sites were not detected in the proviral DNA in either cell line; therefore, the whole cell DNA preparations isolated from each were digested to completion with EcoRI, centrifuged in sucrose gradients and fractions corresponding to 8-15 kb were pooled, dialyzed and concentrated by ethanol precipitation. The bacteriophage λ derivative cloning vector, EMBL-4 (see Karn et al., *Methods Enzymol.* (1983) 101:3-19) was digested to completion with a mixture of EcoRI, BamHI and SalI restriction enzymes and the DNA then deproteinized by phenol-chloroform extraction, precipitated with cold ethanol and resuspended in ligation buffer. (The brief alcohol precipitation selectively recovers large DNA fragments (e.g., phage arms) while the small linker DNA is retained in solution; SalI/SalI filler fragments are not incorporated into the construct during subsequent ligation.) The EMBL-4 phage DNA and EcoRI digest of cellular DNA are mixed and ligated, and the resultant recombinant phage genomes packaged in vitro. After phage infection of λ-sensitive *E coli*, phage plaques were transferred to nitrocellulose filters, DNA was fixed and the filters were screened with FeLV-specific radiolabeled probe as above. Positive plaques, consisting of phage containing the entire FeLV-A or C proviral DNAs, together with flanking human (RD-4 cell) DNA, were recovered.

Plasmids pFeC1A and pFeA12A, were then obtained by subcloning the provirus FeLV-C or A, respectively, from EMBL-4 into pBR328. In the case of provirus A, it was inserted into the SstI/EcoRI site of the $cam^R$ gene, while in the case of C, the provirus was inserted into the EcoRI site of the $cam^R$ gene, with the resulting plasmids being $cam^S$, $amp^R$ and $tet^R$.

Two strategies were then implemented for the construction of hybrid retrovirus proviral plasmids containing the structural gene(s) of either FeLV-A or C and the previously modified LTRs of FeLV-B. (See FIG. 5 for a schematic of the protocol for these constructions.) In the first method, plasmid RF3 was completely digested with SstI and SstII and treated with alkaline phosphatase. pFeC1A and pFeA12A were digested with SstI and SstII to provide fragments (gel isolated) including a portion of the pol gene, and the env gene. The fragments were then inserted into the larger SstI/SstII fragment from RF3 having the amp and cam genes, as well as the partial 1-LTR and deleted r-LTR, to provide plasmids RFCΔS1-B3L or RFAΔS1-B3L (selected using an appropriate probe for the insert). These plasmids were then digested with SstI, treated with alkaline phosphatase and an SstI fragment (gel isolated) containing the gag gene and a portion of the pol gene from pFeC1A and pFeA12A were each inserted to provide plasmids RFCB3L and RFAB3L (probe-selected), which contain the intact structural genes of FeLV-C and FeLV-A, respectively, with the partial 1-LTR and deletion containing r-LTR from RF3 and as occur in RF3X.

For the second procedure, the plasmids RFCΔS1-B3L and RFAΔS I-B3L obtained above (containing the env gene and part of the pol gene of FeLV-C and A, respectively) were digested with the restriction enzymes SstI and XhoI and then isolated by gel electrophoresis. The resultant larger fragments containing the $cam^R$ and $amp^R$ genes were then each ligated to an SstI/XhoI fragment (containing a part of the FeLV-B pol gene) obtained by similar SstI and XhoI digestion of pKC125 followed by gel isolation. The resultant plasmids (p(C)-BΔ, p(A)-BΔ) were then each digested with SstI, treated with alkaline phosphatase and ligated to a gel isolated SstI fragment derived from pKC125 and containing the gag gene and a portion of the pol gene of FeLV-B. The plasmids provided, designated pC-BΔ and pA-BΔ, each contain the partial 1-LTR and deleted r-LTR of FeLV-B (from RF3 and as occur in RF3X) and the intact FeLV-B gag and pol genes, but the C and A env genes, and therefore immunogenicity, of FeLV-C and A, respectively.

Each hybrid proviral plasmid, containing the modified LTRs of FeLV-B and either all the structural genes (method 1 or the env gene only (method 2) of FeLV-A or C, was then utilized to infect susceptible tissue culture cells to produce modified hybrid FeLV viruses and either modified, hybrid, proviral DNA or virus used as a vaccine against FeLV-A or C infection. Similar constructions are applicable to both possible, additional FeLV subgroups and other pathological feline viruses, e.g., feline rhinotracheitis virus, feline infectious peritonitis virus etc.

The subject data showed that the LTRs of retroviruses, including oncornaviruses, can be modified to reduce replication capability, while retaining infectivity, so as to provide effective vaccines for mammalian or avian hosts subject to infection by such viruses. Particularly, by modifying the enhancer region in the LTR, preferably by a deletion of at least about 5 bases and modification of the other LTR to prevent complementarity, i.e., the reversion to wild-type activity by recombination, the infectivity can be retained and an immune response achieved by infecting (e.g., injection, inoculation) mammalian or avian hosts with either the modified viral DNA (proviral plasmid) or modified virus derived therefrom. In this manner, the host is exposed to the viral proteins in their normal environment to ensure that the immune response is activated toward the proper determinants of the wild-type virus. Furthermore, hybrid viral DNAs or viruses can be constructed containing the modified LTRs of one virus and at least the envelope gene(s) of another virus or other gene from a pathogen to provide an immune response, where reduced pathogenicity is dictated by the components of the first virus, but the immunogenicity is dictated by the exogenous gene. Such hybrid, modified viral DNA or viruses provide similar vaccines for mammalian or avian hosts susceptible to infection by the foreign pathogen.

D. VACCINE TRIALS

D.1 Animals

Newborn kittens were obtained from U.C. Davis (Dr. Quentin Rogers, School of Veterinary Medicine and Dr. Murray Gardner, School of Medicine). Each cat had an identification number on its left ear.

D.2. Materials

Recombinant env A was synthesized in yeast and purified as previously described (Sections B.3 and B.6). Attenuated FeLV-A(ΔA) virus was prepared by transfecting tissue culture cells (see Sections C.2–C.6) with plasmid pA-BΔ (see Section C.8) which contains the env A gene instead of the env B gene in a FeLV-B deleted virus.

D.3 Inoculation of Cats

Kittens were divided into four groups each of which received a different immunization program as indicated below:

| Group No. | No. of Kittens | IMMU-NIZATION (DAY 0) | Boost (Day 14 or 19) | Challenge (Day 28 or 32) |
|---|---|---|---|---|
| 1 | 10 | 325 μg env A | ~$10^4$ particles A-Δ virus | $10^5$ particles wild type A virus |
| 2 | 5 | none | ~$10^4$ particles A-Δ virus | $10^5$ particles wild type A virus |
| 3 | 5 | 325 μg env A | 325 μg env A | $10^5$ particles wild type A virus |
| 4 | 5 | none | none | $10^5$ particles wild type A virus |

Kittens were bled at days 9, 17 and 32 post challenge or days 14, 24 and 38 post challenge.

D.4. Protection from Viremia in env A/A-Δ Immunized Kittens

Viremia was determined using the method of Lutz, et al., *J. Immunol. Methods* (1983) 56:209–220 which detects the presence of viral p27 in the blood. Kittens showing detectable levels of p27 were scored as positive (+); kittens showing non-detectable levels of p27 were scored as negative (−). If samples were not submitted to testing they were scored as not determined: (N/D).

Table 2 shows results obtained in these studies. Kittens immunized with env A/Δ-A virus are completely protected from challenge with the wild type virus (5/5 cats) when compared to the control group in which 6/9 kittens were viremic. The deleted virus alone does not protect from viremia (4/5 cats are viremic). Moreover if a 10-fold higher dose of the Δ-A virus is used in 6–8 week old kittens, 8/9 of the cats become viremic.

TABLE 2

Viremia in immunized kittens.

| | \multicolumn{6}{c}{DAYS Post-Challenge} |
|---|---|---|---|---|---|---|
| | 9 | 14 | 17 | 24 | 32 | 38 |
| Group 1: env A/A-delta virus | | | | | | |
| 770 | | | | | | |
| 771 | | − | | − | − | |
| 773 | | − | | − | − | |
| 776 | | − | | − | − | |
| 777 | | − | | − | − | |
| 284 | | − | | − | − | |
| 235 | | − | | − | − | |
| 248 | | − | | − | − | |
| 274 | | − | | − | − | |
| 275 | | − | | +/− | − | |
| Group 2: A-delta virus | | | | | | |
| 738 | − | | − | | + | |
| 739 | + | | + | | + | |
| 775 | + | | + | | + | |
| 778 | − | | − | | − | |
| 779 | + | | + | | + | |
| Group 3: env A/env A | | | | | | |
| 233 | | − | | + | | − |
| 255 | | + | | + | | + |
| 267 | | − | | − | | − |
| 270 | | − | | − | | − |
| 277 | | − | | + | | + |
| Group 4: Controls | | | | | | |
| 736 | − | | + | | + | |
| 745 | − | | − | | + | |
| 762 | − | | − | | − | |
| 774 | − | | + | | + | |
| 272 | ND | | − | | − | |
| 276 | − | | − | | + | |
| 280 | − | | + | | + | |
| 281 | ND | | + | | + | |
| 284 | − | | − | | − | |

It is evident from the above results, that in accordance with the subject invention, mammals can be protected from retroviral pathogenesis by employing a series of inoculations or vaccinations involving priming vaccinations with polypeptides providing for cross-reactivity with at least one epitopic site of an envelope protein followed by infection with an attenuated retrovirus, where the attenuation involves debilitation of the transcriptional regulatory system, particularly the enhancer, so that while the virus may still replicate, it is much more susceptible to control by the immune system of the host.

Although the foregoing invention has been described in some detail by way of illustration and example for purposes of clarity of understanding, it will be obvious that certain changes and modifications may be practiced within the scope of the appended claims.

What is claimed is:

1. A method for protecting a feline host from a feline leukemia virus infection which comprises:
   administering to the feline host in an amount sufficient to elicit an immune response, at least one polypeptide cross-reactive with an epitopic site of an envelope protein of at least one of the serotypes of feline leukemia virus; and
   administering to the feline host the feline leukemia virus attenuated by debilitation of the transcriptional regulatory system.

2. A method according to claim 1, wherein said debilitation results from an uncomplemented mutation in the enhancer region of the LTR of said virus.

3. A method according to claim 2, wherein at least five bases are removed from the enhancer regions of the LTRs of said virus.

4. A method according to claim 1, wherein said feline leukemia virus is proviral DNA.

5. A method according to claim 1, wherein said feline leukemia virus is viral RNA.

6. A method for protecting a feline host from a feline leukemia virus infection which comprises:
   administering to the feline host in an amount sufficient to elicit an immune response, at least one polypeptide cross-reactive with an epitopic site of at least one envelope protein of at least one of the serotypes of feline leukemia virus; and
   administering to the feline host feline leukemia virus having an uncomplemented lesion of at least five bases in the left LTR, wherein said epitopic site and said leukemia virus are from the same or different serotypes.

7. A method according to claim 6, wherein said polypeptide and said feline leukemia virus are both from the same serotype.

8. A method according to claim 7, wherein said serotype is A.

9. A vaccine for protecting a feline host from feline leukemia virus infection, said vaccine comprising, in combination, at least one polypeptide cross-reactive with an epitopic site of an envelope protein of at least one of the serotypes of feline leukemia virus and said feline leukemia virus attenuated by debilitation of the transcriptional regulatory system.

10. A vaccine according to claim 9, wherein said feline leukemia virus is attenuated by debilitation by an uncomplemented mutation in the enhancer region of the LTR of said feline leukemia virus.

11. A vaccine according to claim 10, wherein said uncomplemented mutation is a lesion of at least five bases in the left LTR.

12. A vaccine according to claim 9, wherein said polypeptide and said feline leukemia virus are both from serotype A.

13. A vaccine according to claim 9, wherein said polypeptide and said attenuated feline leukemia virus are formulated in a physiologically acceptable carrier.

* * * * *